(12) United States Patent
Bunce et al.

(10) Patent No.: US 10,945,831 B2
(45) Date of Patent: Mar. 16, 2021

(54) ASYMMETRIC TISSUE GRAFT

(71) Applicant: MUSCULOSKELETAL TRANSPLANT FOUNDATION, Edison, NJ (US)

(72) Inventors: Antonio M. Bunce, Northampton, PA (US); Todd J. Nilsen, Howell, NJ (US); Evangelia Chnari, Scotch Plains, NJ (US); Aldona J. Spiegel, Houston, TX (US); Michael Locarno, Kinnelon, NJ (US); Gregory P. Adams, Wall, NJ (US)

(73) Assignees: Musculoskeletal Transplant Foundation, Edison, NJ (US); The Methodist Hospital, Houston, TX (US)

( * ) Notice: Subject to any disclaimer, the term of this patent is extended or adjusted under 35 U.S.C. 154(b) by 76 days.

(21) Appl. No.: 15/173,286

(22) Filed: Jun. 3, 2016

(65) Prior Publication Data

US 2017/0348088 A1 Dec. 7, 2017

(51) Int. Cl.
*A61F 2/12* (2006.01)
*A61F 2/10* (2006.01)

(52) U.S. Cl.
CPC ............... *A61F 2/12* (2013.01); *A61F 2/105* (2013.01)

(58) Field of Classification Search
CPC .......... A61F 2/12; A61F 2/105; A61F 2/0063
See application file for complete search history.

(56) References Cited

U.S. PATENT DOCUMENTS 4,627,429 A 12/1986 Tsuk
4,776,853 A 10/1988 Klement et al.
(Continued)

FOREIGN PATENT DOCUMENTS

AU 201911154 4/2019
AU 2019043393 6/2019
(Continued)

OTHER PUBLICATIONS

Shuster et al. The Influence of Age and Sex on Skin Thickness, Skin Collagen and Density. British Journal of Dermatology. v93, (1975) p. 639-643.*

(Continued)

*Primary Examiner* — Jerrah Edwards
*Assistant Examiner* — Rokhaya Diop
(74) *Attorney, Agent, or Firm* — Marcella M. Bodner; Cole Schotz, P.C.

(57) ABSTRACT

A dermal tissue allograft includes a dermal matrix having a profile including first and second vertices, a first imaginary axis extending between the first and second vertices, a first peripheral edge extending along a continuous path from the first vertex to the second vertex on a first side of the first imaginary axis, and a second peripheral edge extending along a continuous path from the first vertex to the second vertex on a second side of the first imaginary axis. The first peripheral edge includes an apogee, a convex portion, and a concave portion. The convex and concave portions meet at a transition point located on the first peripheral edge between its apogee and the second vertex. The second peripheral edge includes an apogee and is convex. The second perpendicular distance is greater than the first perpendicular distance. The dermal matrix has a substantially uniform thickness across its profile.

14 Claims, 14 Drawing Sheets

(56) References Cited

U.S. PATENT DOCUMENTS

| | | |
|---|---|---|
| D298,355 S | 11/1988 | Young |
| 4,917,112 A | 4/1990 | Katt |
| 5,314,471 A | 5/1994 | Brauker et al. |
| 5,336,616 A | 8/1994 | Livesey et al. |
| 5,344,454 A | 9/1994 | Clarke et al. |
| 5,453,278 A | 9/1995 | Chan et al. |
| 5,545,223 A | 8/1996 | Neuenfeldt et al. |
| 5,593,440 A | 1/1997 | Brauker et al. |
| 5,653,756 A | 8/1997 | Clarke et al. |
| 5,713,888 A | 2/1998 | Neunfeldt et al. |
| 5,733,336 A | 3/1998 | Neunfeldt et al. |
| 5,741,330 A | 4/1998 | Brauker et al. |
| 5,782,912 A | 7/1998 | Brauker et al. |
| 5,800,529 A | 9/1998 | Brauker et al. |
| D404,134 S | 1/1999 | Dunshee |
| 5,882,354 A | 3/1999 | Brauker et al. |
| 5,964,804 A | 10/1999 | Brauker et al. |
| 6,293,970 B1 | 9/2001 | Wolfinbarger et al. |
| D452,121 S | 12/2001 | Teichelman |
| 6,497,875 B1 | 12/2002 | Sorrell |
| 6,616,685 B2 | 9/2003 | Rousseau |
| 6,734,018 B2 | 5/2004 | Wolfinbarger et al. |
| 6,743,574 B1 | 6/2004 | Wolfinbarger et al. |
| 6,773,458 B1 | 8/2004 | Brauker et al. |
| 6,866,686 B2 | 3/2005 | Ollerenshaw et al. |
| 6,933,326 B1 | 8/2005 | Griffey et al. |
| 7,049,478 B1 | 5/2006 | Smith |
| D537,948 S | 3/2007 | Smith |
| 7,358,284 B2 | 4/2008 | Griffey et al. |
| 7,476,249 B2 | 1/2009 | Frank |
| 7,582,309 B2 | 9/2009 | Rosenberg et al. |
| D609,802 S | 2/2010 | Harren |
| 7,723,108 B2 | 5/2010 | Truncale et al. |
| 7,799,325 B2 | 9/2010 | Kleinsek et al. |
| 7,875,074 B2 | 1/2011 | Chen et al. |
| 7,927,414 B2 | 4/2011 | Yang et al. |
| 8,007,531 B2 | 8/2011 | Frank |
| 8,067,149 B2 | 11/2011 | Livesey et al. |
| 8,197,542 B2 | 6/2012 | Becker |
| 8,202,317 B2 | 6/2012 | Becker |
| 8,263,101 B2 | 9/2012 | Owens et al. |
| 8,268,361 B2 | 9/2012 | Ahlfors |
| 8,324,449 B2 | 12/2012 | McQuillan et al. |
| 8,343,717 B2 | 1/2013 | Owens et al. |
| 8,415,159 B2 | 4/2013 | Ward et al. |
| 8,425,600 B2 | 4/2013 | Maxwell |
| D683,858 S | 6/2013 | Smith |
| 8,486,616 B2 | 7/2013 | Owens et al. |
| 8,557,581 B2 | 10/2013 | Ngo et al. |
| 8,563,232 B2 | 10/2013 | Wolfinbarger et al. |
| 8,563,234 B2 | 10/2013 | Tousimis |
| D693,888 S | 11/2013 | Webster |
| 8,623,398 B2 | 1/2014 | Altman et al. |
| 8,628,791 B2 | 1/2014 | Altman et al. |
| 8,633,027 B2 | 1/2014 | Altman et al. |
| 8,685,426 B2 | 4/2014 | Altman et al. |
| D705,429 S | 5/2014 | Cheney |
| 8,735,054 B1 | 5/2014 | Sun et al. |
| 8,746,014 B2 | 6/2014 | Montarino |
| 8,758,781 B2 | 6/2014 | Ward et al. |
| 8,764,824 B2 | 7/2014 | Ledergerber |
| 8,764,825 B2 | 7/2014 | Ledergerber |
| 8,777,965 B2 | 7/2014 | Chen |
| 8,784,486 B2 | 7/2014 | Schnuessler |
| 8,784,499 B2 | 7/2014 | Owens et al. |
| 8,802,920 B2 | 8/2014 | McQuillan et al. |
| 8,858,629 B2 | 10/2014 | Moses et al. |
| 8,858,647 B2 | 10/2014 | Markman |
| 8,876,899 B2 | 11/2014 | Maxwell |
| 8,916,742 B2 | 12/2014 | Smith |
| 8,936,651 B2 | 1/2015 | Yang |
| 8,986,377 B2 | 3/2015 | Richter et al. |
| 9,027,213 B2 | 5/2015 | Tousimis |
| 9,050,177 B2 | 6/2015 | Markman |
| 9,066,884 B2 | 6/2015 | Altman et al. |
| 9,078,731 B2 | 7/2015 | Montarino |
| 9,089,501 B2 | 7/2015 | Altman |
| 9,089,523 B2 | 7/2015 | Xu et al. |
| 9,114,003 B2 | 8/2015 | Kalus |
| 9,150,318 B1 | 10/2015 | Sun et al. |
| 9,162,011 B2 | 10/2015 | Stillwell et al. |
| 9,180,143 B2 | 11/2015 | Bolland et al. |
| 9,199,002 B2 | 12/2015 | Mao et al. |
| 9,204,953 B2 | 12/2015 | Mortarino |
| 9,204,954 B2 | 12/2015 | Mortarino |
| 9,206,442 B2 | 12/2015 | Chen |
| 9,220,259 B2 | 12/2015 | Owens et al. |
| 9,238,793 B2 | 1/2016 | Chen et al. |
| 9,271,821 B2 | 3/2016 | Roock et al. |
| 9,277,986 B2 | 3/2016 | Moses et al. |
| 9,308,070 B2 | 4/2016 | Mortarino |
| 9,326,840 B2 | 5/2016 | Mortarino |
| 9,336,435 B1 | 5/2016 | Ozog |
| 9,351,819 B2 | 5/2016 | Harper |
| 9,370,536 B2 | 6/2016 | Sun et al. |
| 9,375,017 B2 | 6/2016 | Hazylett et al. |
| 9,375,513 B2 | 6/2016 | Sun et al. |
| 9,382,422 B2 | 7/2016 | Owens |
| 9,426,980 B2 | 8/2016 | Tousimis |
| 9,504,770 B2 | 11/2016 | Xu et al. |
| 9,532,863 B2 | 1/2017 | Hayzlett |
| 9,532,866 B2 | 1/2017 | Kim et al. |
| 9,539,086 B2 | 1/2017 | Schuessler et al. |
| 9,549,805 B2 | 1/2017 | Hazylett et al. |
| 9,549,812 B2 | 1/2017 | Shetty et al. |
| 9,579,420 B2 | 2/2017 | Wolfinbarger et al. |
| 9,585,744 B2 | 3/2017 | Moses et al. |
| 9,585,986 B2 | 3/2017 | Wolfinbarger et al. |
| 9,592,254 B2 | 3/2017 | Monteiro et al. |
| 9,592,278 B2 | 3/2017 | Sun et al. |
| 9,622,845 B2 | 4/2017 | Markman |
| 9,636,435 B2 | 5/2017 | Sun et al. |
| 9,681,941 B2 | 6/2017 | Griffin et al. |
| 9,782,436 B2 | 10/2017 | Sun |
| 9,808,338 B2 | 11/2017 | Schuessler |
| 9,888,999 B2 | 2/2018 | Forsell et al. |
| 9,901,440 B2 | 2/2018 | Liu et al. |
| 9,936,688 B2 | 4/2018 | Wolfinbarger et al. |
| 9,956,072 B2 | 5/2018 | Diaz et al. |
| 9,956,316 B2 | 5/2018 | Chen |
| 9,957,477 B2 | 5/2018 | Chen et al. |
| 9,999,637 B2 | 6/2018 | Owens et al. |
| 10,004,590 B2 | 6/2018 | Shetty et al. |
| 10,022,214 B2 | 7/2018 | Hayzlett |
| 10,039,633 B2 | 8/2018 | Ansorge et al. |
| RE47,100 E | 10/2018 | Smith |
| D841,172 S | 2/2019 | Bannwart |
| 10,231,874 B2 | 3/2019 | Mumby |
| 10,238,485 B2 | 3/2019 | Locarno et al. |
| D851,261 S | 6/2019 | Ricks |
| D856,517 S | 8/2019 | Spiegel et al. |
| D875,957 S | 2/2020 | Bannwart |
| D876,645 S | 2/2020 | Zhang |
| D876,646 S | 2/2020 | Kase |
| D879,978 S | 3/2020 | Bannwart |
| 2003/0083752 A1 | 5/2003 | Wolfinbarger et al. |
| 2004/0162512 A1 | 8/2004 | Liedtke |
| 2004/0260315 A1 | 12/2004 | Dell et al. |
| 2005/0028228 A1 | 2/2005 | McQuillan et al. |
| 2005/0186286 A1 | 8/2005 | Takami |
| 2005/0246035 A1 | 11/2005 | Wolfinbarger et al. |
| 2006/0210960 A1 | 9/2006 | Livesey et al. |
| 2007/0207125 A1 | 9/2007 | Bothwell et al. |
| 2007/0244568 A1 | 10/2007 | Matsuda et al. |
| 2007/0269791 A1 | 11/2007 | Takami et al. |
| 2008/0058692 A1 | 3/2008 | Propp |
| 2008/0097601 A1 | 4/2008 | Codori-Hurff et al. |
| 2008/0154366 A1* | 6/2008 | Frank ............ A61F 2/0063 623/8 |
| 2008/0281419 A1 | 11/2008 | Matheny et al. |
| 2009/0065014 A1 | 3/2009 | Nagata |
| 2009/0198332 A1 | 8/2009 | Becker |
| 2009/0198333 A1 | 8/2009 | Becker |
| 2009/0312685 A1 | 12/2009 | Olsen |

(56) References Cited

U.S. PATENT DOCUMENTS

| | | |
|---|---|---|
| 2010/0003306 A1 | 1/2010 | Von Waldburg-Zeil |
| 2010/0010627 A1 | 1/2010 | Matheny |
| 2010/0028396 A1 | 2/2010 | Ward et al. |
| 2010/0040687 A1 | 2/2010 | Pedrozo et al. |
| 2010/0067106 A1 | 3/2010 | Woker et al. |
| 2010/0082048 A1 | 4/2010 | Granja |
| 2010/0112543 A1 | 5/2010 | Ngo et al. |
| 2010/0191330 A1 | 7/2010 | Lauryssen et al. |
| 2010/0216206 A1 | 8/2010 | Marzaro |
| 2010/0272782 A1 | 10/2010 | Owens et al. |
| 2010/0285587 A1 | 11/2010 | Ollerenshaw et al. |
| 2010/0310628 A1 | 12/2010 | Waldburg-Zeil |
| 2011/0022171 A1* | 1/2011 | Richter .............. A61F 2/12 623/8 |
| 2011/0035004 A1 | 2/2011 | Maxwell |
| 2011/0054604 A1 | 3/2011 | Becker |
| 2011/0054605 A1 | 3/2011 | Becker |
| 2011/0106249 A1 | 5/2011 | Becker |
| 2011/0167602 A1 | 7/2011 | Altman et al. |
| 2011/0184227 A1 | 7/2011 | Altman et al. |
| 2011/0276039 A1 | 11/2011 | Markman |
| 2011/0288568 A1 | 11/2011 | Capuzziello |
| 2012/0010728 A1 | 1/2012 | Sun et al. |
| 2012/0034191 A1 | 2/2012 | Maltheny |
| 2012/0040013 A1 | 2/2012 | Owens et al. |
| 2012/0053690 A1 | 3/2012 | Frank |
| 2012/0059411 A1 | 3/2012 | Sun et al. |
| 2012/0061004 A1 | 3/2012 | Towler |
| 2012/0065649 A1 | 3/2012 | Towler |
| 2012/0158134 A1 | 6/2012 | Codori-Hurff et al. |
| 2012/0221105 A1 | 8/2012 | Altman et al. |
| 2012/0226352 A1 | 9/2012 | Becker |
| 2012/0263763 A1 | 10/2012 | Sun et al. |
| 2012/0265218 A1 | 10/2012 | Chen et al. |
| 2012/0276213 A1 | 11/2012 | Chen |
| 2012/0283826 A1 | 11/2012 | Moses et al. |
| 2012/0310367 A1 | 12/2012 | Connor |
| 2012/0329034 A1 | 12/2012 | Chun et al. |
| 2013/0013068 A1 | 1/2013 | Forsell et al. |
| 2013/0103061 A1 | 4/2013 | Harper |
| 2013/0121970 A1 | 5/2013 | Owens et al. |
| 2013/0144356 A1 | 6/2013 | Horn et al. |
| 2013/0156744 A1 | 6/2013 | Taylor et al. |
| 2013/0158658 A1 | 6/2013 | Hayzlett |
| 2013/0211519 A1 | 8/2013 | Dempsey |
| 2013/0224260 A1 | 8/2013 | Ward et al. |
| 2013/0287741 A1 | 10/2013 | Stillwell et al. |
| 2013/0317610 A1 | 11/2013 | Ledergerber |
| 2014/0081397 A1 | 3/2014 | Kalus |
| 2014/0100656 A1 | 4/2014 | Namnoum et al. |
| 2014/0257481 A1 | 9/2014 | Brooks et al. |
| 2014/0257482 A1 | 9/2014 | Ward et al. |
| 2014/0276957 A1 | 9/2014 | Locarno et al. |
| 2014/0296623 A1 | 10/2014 | Owens et al. |
| 2014/0335144 A1 | 11/2014 | Ward et al. |
| 2015/0012089 A1 | 1/2015 | Shetty et al. |
| 2015/0037436 A1 | 2/2015 | Huang et al. |
| 2015/0150674 A1 | 6/2015 | Ansorge et al. |
| 2015/0157451 A1 | 6/2015 | Bowley et al. |
| 2015/0159066 A1 | 6/2015 | Hartwell |
| 2015/0209128 A1 | 7/2015 | Markman |
| 2015/0223928 A1* | 8/2015 | Limem .............. A61F 2/12 623/8 |
| 2015/0250582 A1* | 9/2015 | Greenhalgh .............. A61F 2/12 623/8 |
| 2015/0297798 A1 | 10/2015 | Badylak et al. |
| 2015/0320911 A1 | 11/2015 | Sun et al. |
| 2015/0351891 A1 | 12/2015 | Moses et al. |
| 2016/0000097 A1 | 1/2016 | Rosines |
| 2016/0000970 A1 | 1/2016 | Rosines |
| 2016/0022416 A1 | 1/2016 | Felix et al. |
| 2016/0030487 A1 | 2/2016 | Bachrach et al. |
| 2016/0030636 A1 | 2/2016 | Muir |
| 2016/0045198 A1 | 2/2016 | Bachrach |
| 2016/0067106 A1 | 3/2016 | Howell |
| 2016/0135940 A1 | 5/2016 | Roock et al. |
| 2016/0151062 A1 | 6/2016 | Bachrach |
| 2016/0199173 A1 | 7/2016 | Liu |
| 2016/0256259 A1 | 9/2016 | Wirth et al. |
| 2016/0256606 A1 | 9/2016 | Sun et al. |
| 2016/0262835 A1 | 9/2016 | Davila et al. |
| 2016/0271295 A1 | 9/2016 | Sun et al. |
| 2016/0287747 A1 | 10/2016 | Schallenberger |
| 2016/0331504 A1* | 11/2016 | Wang .............. A61F 2/0063 |
| 2017/0007394 A1 | 1/2017 | Shetty et al. |
| 2017/0021058 A1 | 1/2017 | Huang et al. |
| 2017/0049549 A1 | 2/2017 | Bayat et al. |
| 2017/0049929 A1 | 2/2017 | Xu et al. |
| 2017/0049932 A1 | 2/2017 | Badylak et al. |
| 2017/0065742 A1 | 3/2017 | Sun et al. |
| 2017/0071273 A1 | 3/2017 | Barere et al. |
| 2017/0072110 A1 | 3/2017 | Ringo |
| 2017/0143475 A1 | 3/2017 | Moses et al. |
| 2017/0100509 A1 | 4/2017 | Sun et al. |
| 2017/0189165 A1 | 7/2017 | Hristov |
| 2017/0202661 A1 | 7/2017 | Griffin et al. |
| 2017/0209619 A1 | 7/2017 | Monteiro et al. |
| 2017/0216008 A1 | 8/2017 | Markman |
| 2017/0216009 A1 | 8/2017 | Felix |
| 2017/0224460 A1 | 8/2017 | Ringo |
| 2017/0224869 A1 | 8/2017 | Shah et al. |
| 2017/0231753 A1 | 8/2017 | Lee |
| 2017/0281333 A1 | 10/2017 | Locarno et al. |
| 2017/0340437 A1 | 11/2017 | Bowley |
| 2017/0348088 A1 | 12/2017 | Bunce |
| 2017/0348353 A1 | 12/2017 | Sun |
| 2017/0348460 A1 | 12/2017 | Fang et al. |
| 2017/0367807 A1 | 12/2017 | Chen et al. |
| 2018/0008745 A1 | 1/2018 | Park et al. |
| 2018/0044629 A1 | 2/2018 | Qin |
| 2018/0055624 A1 | 3/2018 | Barere et al. |
| 2018/0092737 A1 | 4/2018 | Barere et al. |
| 2018/0110612 A1 | 4/2018 | Schuessler et al. |
| 2018/0214262 A1 | 8/2018 | Diaz et al. |
| 2018/0214607 A1 | 8/2018 | Chen |
| 2018/0216062 A1 | 8/2018 | Chen et al. |
| 2018/0221136 A1 | 8/2018 | Kaplan |
| 2018/0264037 A1 | 9/2018 | Owens et al. |
| 2018/0280132 A1 | 10/2018 | Shetty et al. |
| 2018/0333252 A1 | 11/2018 | Ansorge et al. |
| 2020/0054429 A1 | 2/2020 | Towfigh |
| 2020/0078165 A1 | 3/2020 | Spiegel |

FOREIGN PATENT DOCUMENTS

| | | |
|---|---|---|
| CA | 186423 | 3/2019 |
| CA | 3053144 | 8/2019 |
| CN | 104640577 A | 5/2015 |
| EP | 2692363 A1 | 2/2014 |
| EP | 2692364 A1 | 2/2014 |
| EP | 2926840 A1 | 10/2015 |
| EP | 3034038 | 6/2016 |
| EP | 3056167 A1 | 8/2016 |
| EP | 3056168 A1 | 8/2016 |
| EP | 006280178 | 3/2019 |
| EP | 19190980.3 | 8/2019 |
| FR | 2746298 | 9/1997 |
| WO | 1984/004880 | 12/1984 |
| WO | 1984/004880 A1 | 12/1984 |
| WO | 1999/065470 | 12/1999 |
| WO | 2005/063314 | 7/2005 |
| WO | 2008/066883 | 6/2008 |
| WO | 2008/148026 | 12/2008 |
| WO | 2008/154623 | 12/2008 |
| WO | 20080154623 | 12/2008 |
| WO | 2010/027613 | 8/2009 |
| WO | 2010071624 | 6/2010 |
| WO | 2011/011394 | 1/2011 |
| WO | 2011/019361 | 2/2011 |
| WO | 2012/031162 | 3/2012 |
| WO | 2009/065013 | 4/2013 |
| WO | 2013/106556 | 7/2013 |
| WO | 2013/126062 | 8/2013 |
| WO | 2013126062 A2 | 8/2013 |

(56) References Cited

FOREIGN PATENT DOCUMENTS

| WO | 2013/137664 | 9/2013 |
|---|---|---|
| WO | 2013/192197 | 12/2013 |
| WO | 2014/008184 | 1/2014 |
| WO | 2014/019672 | 2/2014 |
| WO | 2014019672 A1 | 2/2014 |
| WO | 2014/047234 | 3/2014 |
| WO | 2014/145462 | 9/2014 |
| WO | 2014/160008 | 10/2014 |
| WO | 2014/160124 | 10/2014 |
| WO | 2014160008 | 10/2014 |
| WO | 2014160124 A1 | 10/2014 |
| WO | 2015/021807 | 2/2015 |
| WO | 2015/065923 | 5/2015 |
| WO | 2015065923 | 5/2015 |
| WO | 2015/121686 | 8/2015 |
| WO | 2015/164728 | 10/2015 |
| WO | 2015148932 A1 | 10/2015 |
| WO | 2015/176014 | 11/2015 |
| WO | 2016/130559 | 8/2016 |
| WO | 2016/144475 | 9/2016 |
| WO | 2016144475 | 9/2016 |
| WO | 2015/148932 | 10/2018 |
| WO | 2018195476 | 10/2018 |
| WO | 2019157048 | 8/2019 |

OTHER PUBLICATIONS

Butler et al., Reduction of Adhesions with Composite AlloDerm/Polypropylene Mesh Implants for Abdominal Wall Reconstruction, Plast. Reconstr. Surg., (2004), v114, p. 464-473.
Erdag, et al., "Fibroblasts Improve Performance of Cultured Composite Skin Substitutes on Athymic Mice", Burns, 30 (2004), pp. 322-328.
International Search Report and Written Opinion for Applicant's related International (PCT) Application No. PCT/US2014/025619, dated Jun. 30, 2014 (13 pages).
IP Australia, Patent Examination Report No. 1 in Applicant's related Australian Patent Application No. 2014244272, dated Mar. 10, 2016 (3 pages).
Isch et al., Patch Esophagoplasty Using AlloDerm as a Tissue Scaffold. Journal of Pediatric Surgery (2001 ), v36(2), pp. 266-268.
Kolker et al., Multilayer Reconstruction of Abdominal Wall Defects With Acellular Dermal Allograft (AlloDerm) and Component Separation, Annals of Plastic Surgery (2005), v55(1), pp. 36-42.
Leung et al., Skin Grafts, UTMJ (2009), v86(2), pp. 61-64.
New Zealand Intellectual Property Office, First Examination Report in Applicant's related New Zealand Patent Application No. 710330, dated Feb. 25, 2016 (4 pages).
Oliver, et al., "Reconstruction of Full-Thickness Loss Skin Wounds Using Skin Collagen Allografts", British Journal of Plastic Surgery, 32 (1979), pp. 87-90.
Shuster et al., The influence of age and sex on skin thickness, skin collagen and density. British Journal of Dermatology (1975), v96, p. 639-643.
U.S. Appl. No. 15/032,567, filed Apr. 27, 2016 (72 pages).
Applicant's related Design U.S. Appl. No. 29/566,994, filed Jun. 3, 2016 (15 pages).
Ownby (2010), The Integument—the skin and all of its deriviates. U.S. Appl. No. 61/783,237, filed Mar. 14, 2013.
Final Office Action for U.S. Appl. No. 15/621,602, dated Nov. 13, 2017.
Non-Final Office Action for U.S. Appl. No. 15/621,602, dated Aug. 10, 2017.
Office Action in related Canadian Patent Application No. 2,899,642, dated Sep. 13, 2016.
Office Action issued for related European Patent Application No. 14718250.5, dated Nov. 23, 2016.
Patent Examination Report No. 1 in related Australian Patent Application No. 2016234904, dated Apr. 28, 2017.
Mine et al. Aging Alters Functionally Human Dermal Papillary Fibroblasts but not Reticular Fibroblasts: A New View of Skin Morphogenesis and Aging. PLoS One (2008), v3(12), e4066, 13 pages.
Further Examination Report in related New Zealand Patent Application No. 710330, dated Oct. 11, 2016.
Further Examination Report in related New Zealand Patent Application No. 710330, dated Feb. 8, 2017.
Ownby (2010). The Integument—the skin and all of it's derivatives.
U.S. Appl. No. 15/621,602, filed Jun. 13, 2017.
U.S. Appl. No. 14/208,025, filed Mar. 13, 2014.
Restriction Requirement for U.S. Appl. No. 14/208,025, dated Nov. 3, 2015.
Office Action for U.S. Appl. No. 14/208,025, dated Feb. 26, 2016.
Final Office Action for U.S. Appl. No. 14/208,205, dated Aug. 19, 2016.
Office Action for U.S. Appl. No. 14/208,025, dated Mar. 13, 2017.
International Preliminary Report on Patentability for PCT/US2014/025619, dated Sep. 15, 2015.
Office Action in related Canadian Patent Application No. 2,899,642, dated Oct. 24, 2017.
Office Action for U.S. Appl. No. 15/621,602, dated Jul. 12, 2018.
Kesmarky G., et al., "Plasma viscosity: A forgotten variable", Clinical Hemorheology and Microcirculation, 2008, vol. 39, pp. 243-246, IOS Press.
U.S. Appl. No. 15/858,360, filed Dec. 29, 2017.
Li Y., et al., "Experimental validation of non-invasive and fluid density independent methods for the determination of local wave speed and arrival time of reflected wave", Journal of Biomechanics, 2011, vol. 44, pp. 1393-1399, Elsevier.
Mulder G. D., "Quantifying wound fluids for the clinician and researcher", Ostomy / Wound Management, 1994, vol. 40, pp. 65-69.
U.S. Appl. No. 62/440,526, filed Dec. 30, 2016.
Office Action for U.S. Appl. No. 15/858,360 dated May 11, 2018.
U.S. Appl. No. 62/468,511, filed Mar. 8, 2017.
Notice of Allowance for Design U.S. Appl. No. 29/662,750, dated May 14, 2020.
International Search Report and Written Opinion for related International {PCT) Application No. PCT/US2014/025619, dated Jun. 30, 2014.
Design U.S. Appl. No. 29/662,750, filed Sep. 7, 2018.
U.S. Appl. No. 12/964,250, filed Dec. 9, 2010.
U.S. Appl. No. 15/915,412, filed Mar. 8, 2018.
U.S. Appl. No. 16/125,435, filed Sep. 7, 2018.
Design U.S. Appl. No. 29/566,994, filed Jun. 3, 2016.
Non-Final Office Action for U.S. Appl. No. 16/125,435, dated Feb. 28, 2020.
Notice of Allowance for U.S. Appl. No. 16/173,286, dated May 14, 2020.
Partial European Search Report issued for European Patent Application No. 19190980.3, dated Feb. 17, 2020.
Notice of Allowance for U.S. Appl. No. 16/125,435, dated Jun. 22, 2020.

* cited by examiner

FIG. 3
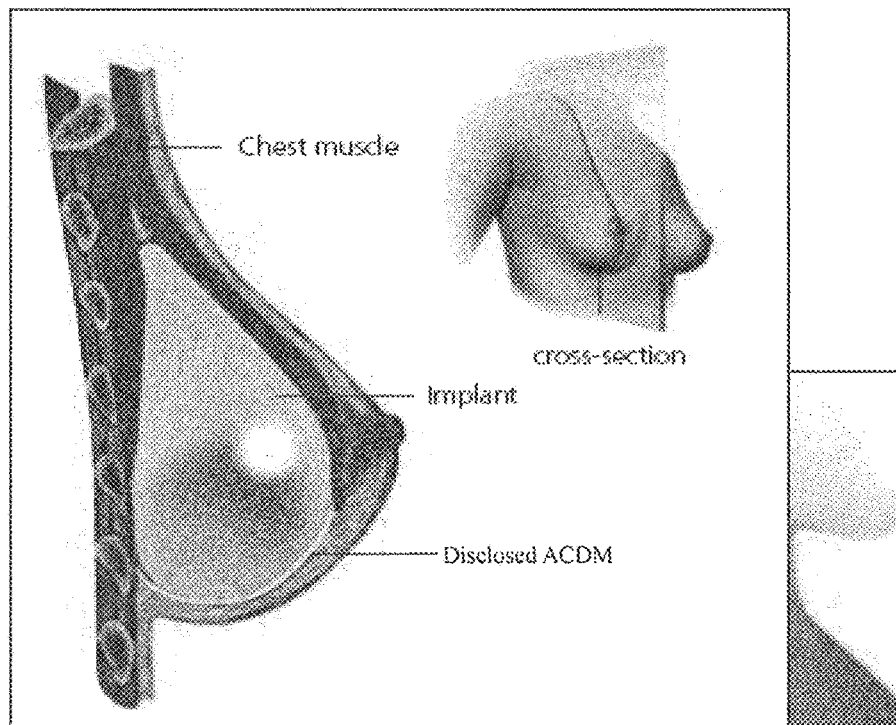
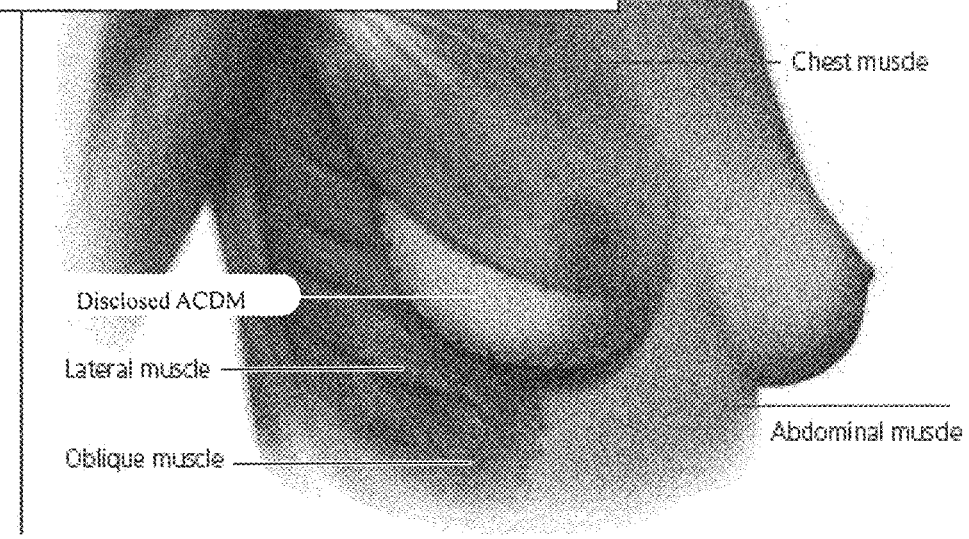
FIG. 4

*error is represented as standard error of the mean (SEM)

FlexHD Structural ACDM epidermal side dermal side

Disclosed ACDM epidermal side dermal side

FlexHD Structural ACDM

Disclosed ACDM

ASYMMETRIC TISSUE GRAFT

FIELD OF THE INVENTION

The present invention relates generally to allografts made from decellularized dermal tissues, and in particular, to the use of such allografts for soft tissue repair, including breast reconstruction and other plastic surgery procedures.

BACKGROUND OF THE INVENTION

Human allograft dermal tissue has been widely accepted for use in various surgical procedures for decades. For example, acellular dermal matrices ("ACDMs") derived from allograft dermal tissue are used in the repair of ventral abdominal hernias and other abdominal wall defects.

Human allograft skin, as illustrated in FIG. 1, is recovered from either live or deceased donors after receiving consent from the individual donor or donor's family. The skin is made of several layer-like components, including the outermost epidermis E, and the dermis D, which lies beneath the epidermis. The hypodermis H (also referred to as the subcutis) lies beneath the dermis D, but is not part of the skin. Rather, the hypodermis H contains adipose and muscle tissue. The dermis D itself includes the papillary dermis PD, which lies adjacent the epidermis E, and the reticular dermis RD, which lies between the papillary dermis PD and the hypodermis H. The papillary-reticular dermis interface PRI, lies between the papillary dermis PD and the reticular dermis RD. The dermis-epidermis junction ("the DEJ") lies between the papillary dermis PD and epidermis E.

The process for deriving the foregoing ACDMs from dermal tissue involves removing the the epidermis E (e.g., by a chemical process that causes the epidermis to slough off), and thereby exposing the DEJ that was adjacent the epidermis E. Beneath the DEJ lies the papillary dermis PD, the papillary-reticular dermal interface PRI, and the reticular dermis RD. The dermal tissue that is recovered for the ACDMs may therefore include the DEJ, papillary dermis PD and at least part of the reticular dermis RD. The recovered dermal tissue is decellularized and aseptically processed to meet sterility testing requirements.

SUMMARY OF THE INVENTION

In an embodiment, a dermal tissue allograft includes a dermal matrix having a profile including a first vertex, a second vertex, a first imaginary axis extending from the first vertex to the second vertex, a first peripheral edge extending along a continuous path from the first vertex to the second vertex on a first side of the first imaginary axis, and a second peripheral edge extending along a continuous path from the first vertex to the second vertex on a second side of the first imaginary axis. The second side is opposite to the first side. The first peripheral edge includes an apogee that is a first perpendicular distance from the first imaginary axis, a convex portion that is convex with respect to the first imaginary axis, and a concave portion that is concave with respect to the first imaginary axis. The convex and concave portions of the first peripheral edge meet at a transition point that is disposed on the first peripheral edge between the apogee of the first peripheral edge and the second vertex. The second peripheral edge includes an apogee that is a second perpendicular distance from the first imaginary axis. The second peripheral edge is convex with respect to the first imaginary axis. The second perpendicular distance is greater than the first perpendicular distance. The dermal matrix has a thickness that is substantially uniform across the profile of the dermal matrix.

In an embodiment, the dermal matrix is an acellular dermal matrix. In an embodiment, the dermal matrix includes a plurality of perforations. In an embodiment, each of the plurality of perforations is substantially circular. In an embodiment, substantially all of the perforations are located between the first imaginary axis and the second peripheral edge. In an embodiment, the apogee of the first peripheral edge and the apogee of the second peripheral edge define a second imaginary axis that is not perpendicular to the first imaginary axis.

In an embodiment, the distance between the first vertex and the second vertex is in a range from about 15 cm to about 24 cm. In an embodiment, the ratio of the distance between the first vertex and the second vertex to the first perpendicular distance is in a range of from about 4.2 to about 5.3. In an embodiment, the ratio of the distance between the first vertex and the second vertex to the second perpendicular distance is in a range of from about 2.4 to about 3.1. In an embodiment, the first perpendicular distance is in a range of from about 30 mm to about 55 mm. In an embodiment, the second perpendicular distance is a range of from about 60 mm to about 95 mm. In an embodiment, the ratio of the second perpendicular distance to the first perpendicular distance is in a range of from about 1.5 to about 2.1. In an embodiment, the thickness of the dermal matrix is in a range of from about 0.5 mm to about 3.0 mm.

In an embodiment, a kit includes two dermal tissue allografts.

BRIEF DESCRIPTION OF THE DRAWINGS

The present invention will be further explained with reference to the attached drawings, wherein like structures are referred to by like numerals and/or letters throughout the several views. The drawings shown are not necessarily to scale, with emphasis instead generally being placed upon illustrating the principles of the present invention.

FIG. 3 is a cross-sectional schematic view of an ACDM being used as a sling for breast reconstruction according to an embodiment of the present invention;

FIG. 4 is a perspective view of an ACDM being used as a sling for breast reconstruction according to an embodiment of the present invention;

DETAILED DESCRIPTION OF THE INVENTION

Detailed embodiments of the present invention are disclosed herein. It should be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, and some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as examples for teaching one skilled in the art to variously employ the present invention.

The present invention generally relates to dermal allografts for use in the repair of soft tissue defects. More particularly, the present invention relates to a flexible, pliable acellular dermis surgical implant, or tissue form, comprising a section cut from a full thickness dermal tissue. The ACDMs of the present invention possess structural and biomechanical properties that are conducive to their use in breast reconstruction and other plastic surgery applications. Such properties include, but are not limited to, predictable suppleness, flexibility, uniform pliability sufficient to stretch and expand without tearing during tissue expansion (i.e., using a breast implant and/or tissue expander), sufficient tensile strength for breast reconstruction and other plastic surgery applications, improved handling properties, and substantially uniform porosity that promotes rapid and efficient cellular ingrowth equally from either side of the ACDM.

In one embodiment of the invention, an ACDM is derived from allograft dermal tissue that is recovered from deeper within the dermis, and is therefore farther from, and not adjacent the epidermis. The procedure for preparing such an ACDM according to one embodiment of the invention is described below.

Figure 1:
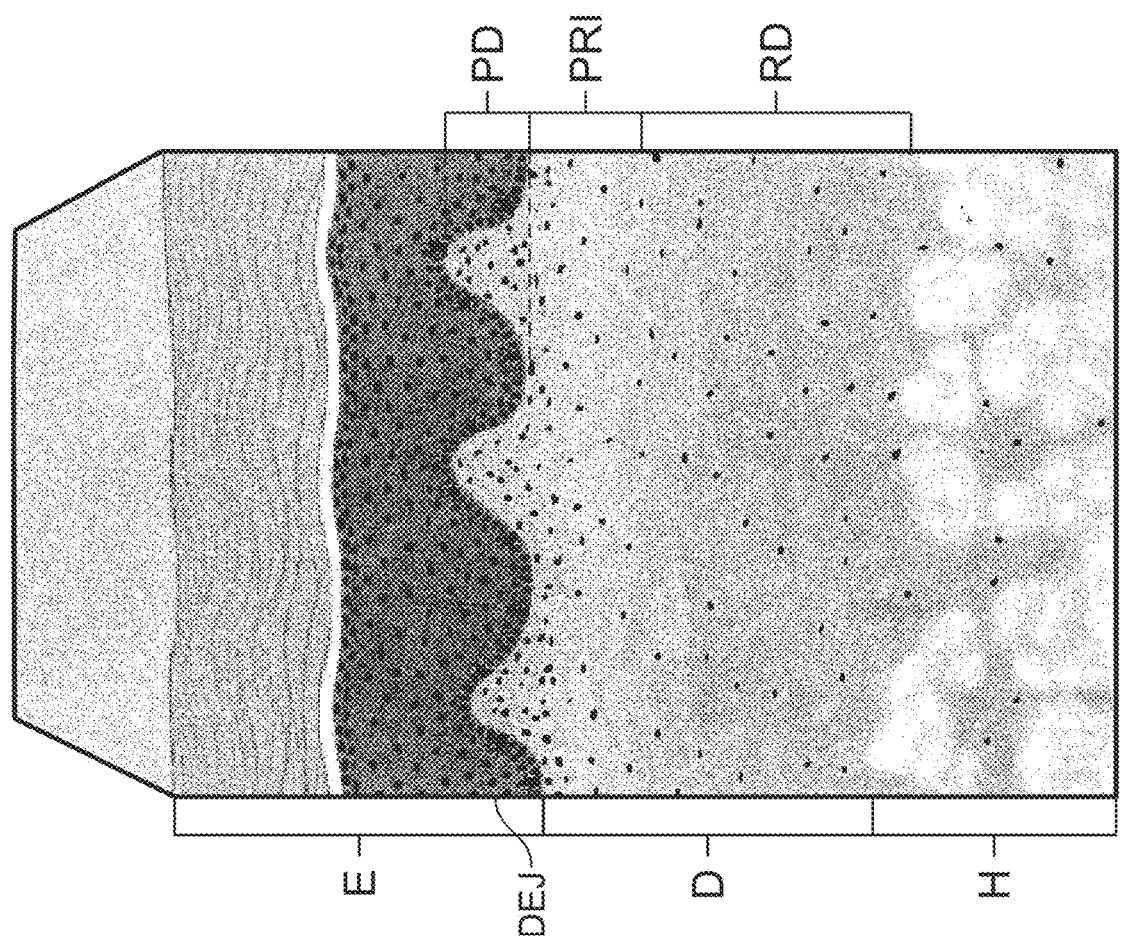
FIG. 1 is a perspective schematic view of a section of human skin and the various components thereof.
Figure 2:
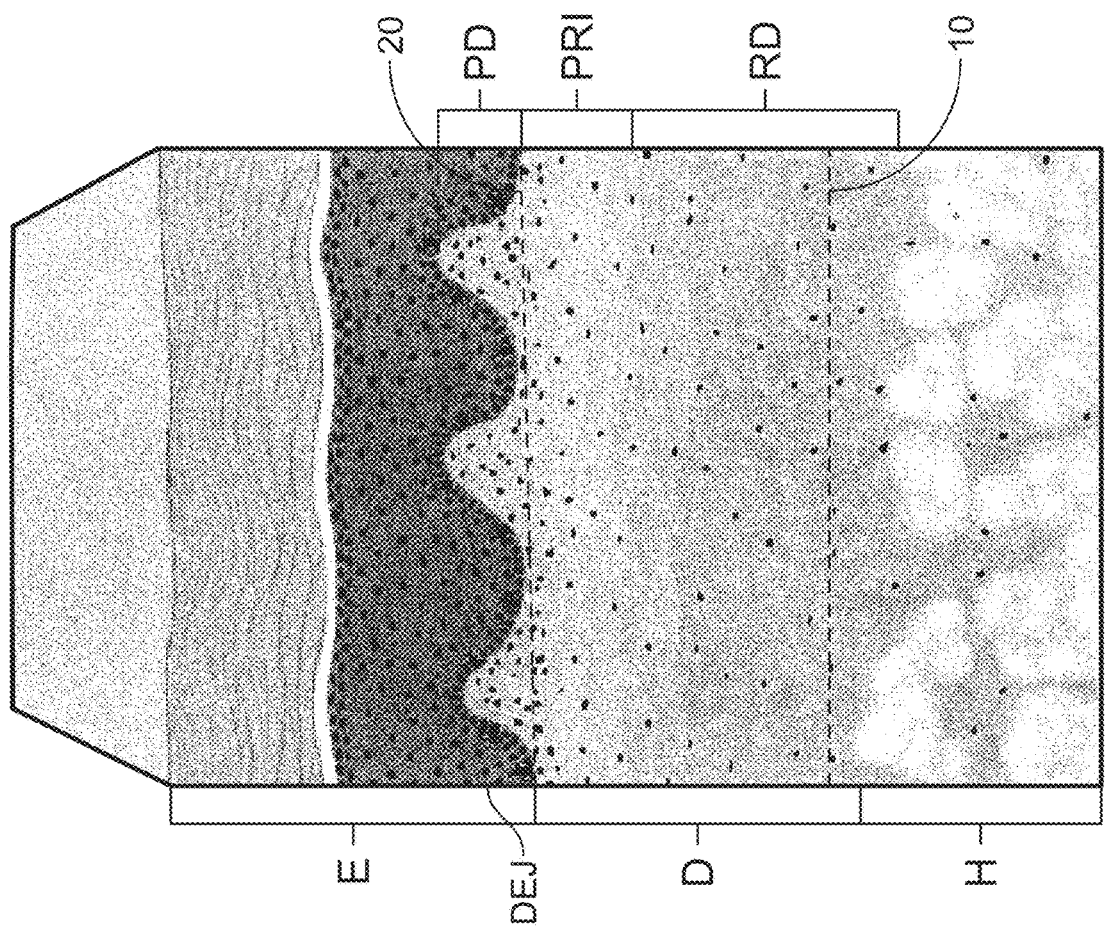
FIG. 2 is a perspective schematic view of the section of human skin shown in FIG. 1, and also illustrates the cutting steps performed on same according to an embodiment of the present invention.

The recovery of portions of the dermis D from the skin may be accomplished by various techniques and devices, such as, for example, a manual dermatome technique, or dissection with a scalpel. In an embodiment illustrated in FIG. 2, a first cut 10 is made into the reticular dermis RD of the skin (e.g., a section of skin cut from the entire donor skin) proximate the underlying hypodermis H in order to remove it from the dermis D. A second cut 20 is then made into the epidermal portion of the papillary dermis PD containing the dense collagen matrix, as discussed in the foregoing Background section, in order to remove the epidermis E, the DEJ, and the underlying epidermal portion of the papillary dermis PD. The remaining portion of the dermis D (i.e., the deeper dermal portion of the papillary dermis PD and the reticular dermis RD) constitutes a collagen matrix having substantially uniform density and porosity.

In one embodiment, the remaining portion of the dermis ("the tissue") is then minimally processed, e.g., according to the process disclosed in U.S. Pat. No. 7,723,108, the disclosure of which is incorporated by reference herein in its entirety. In another embodiment, the tissue is decellularized by chemically treating it with saline, detergent, peracetic acid, ethanol and propylene glycol. The tissue is then washed with sterile water to remove residual processing chemicals. The disinfected and acellular tissue is cut into rectangular-shaped sheets suitable for clinical uses. The tissue sheets are treated with aqueous ethanol and then packaged to provide a hydrated collagen matrix, i.e., the ACDM.

The process(es) used to treat the tissue preserves the extracellular matrix of the dermis. The resulting ACDM thereby provides a framework to support cellular repopulation, vascularization, and tissue regeneration at the surgical site.

The ACDM derived using the process(es) disclosed above (referred to herein as the "Disclosed ACDM") exhibits properties that are ideal for its use as a sling in breast reconstruction, and its use in other plastic surgery applications, as is evident from the Examples presented below. Use of the Disclosed ACDM minimizes adhesions and foreign body reactions while promoting vascularization, cellular attachment, and tissue ingrowth at the surgical site. Compared to the prior art ACDMs (i.e., those discussed in the Background section), the Disclosed ACDM possesses more uniform tensile properties (i.e., strength, pliability, stretchability and handling characteristics) that are optimal for its use in breast reconstruction and other plastic surgery applications. The Disclosed ACDM also possesses improved suture retention strength, and elasticity and deformability that are optimal for its intended use. For example, the improved elasticity of the Disclosed ACDM promotes better expansion of the tissue in breast reconstruction. The Disclosed ACDM is therefore very strong and closely mimics the biomechanical properties of the tissue that it is intended to replace. Further, the Disclosed ACDM is resistant to bacterial colonization and non-immunogenic as a result of the treatment thereto and decellularization thereof.

FIGS. 3 and 4 illustrate use of the ACDM as a sling for breast reconstruction. As shown in these figures, the ACDM conforms to the shape of the breast implant (or tissue expander) in its function as a supportive sling.

Figure 5B:
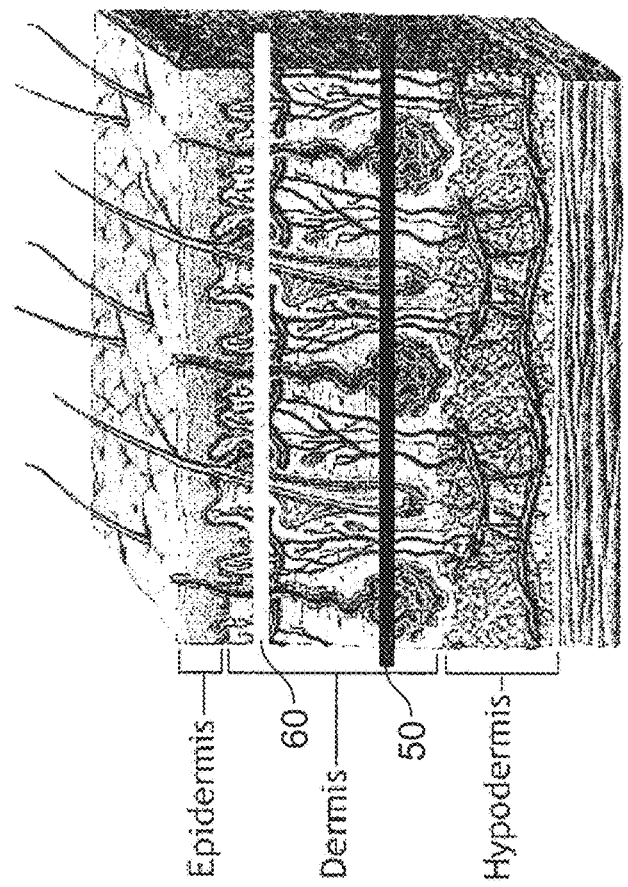
FIG. 5b is a perspective schematic view of a process according to an embodiment of the present invention, as performed on a section of human skin.
Figure 5A:
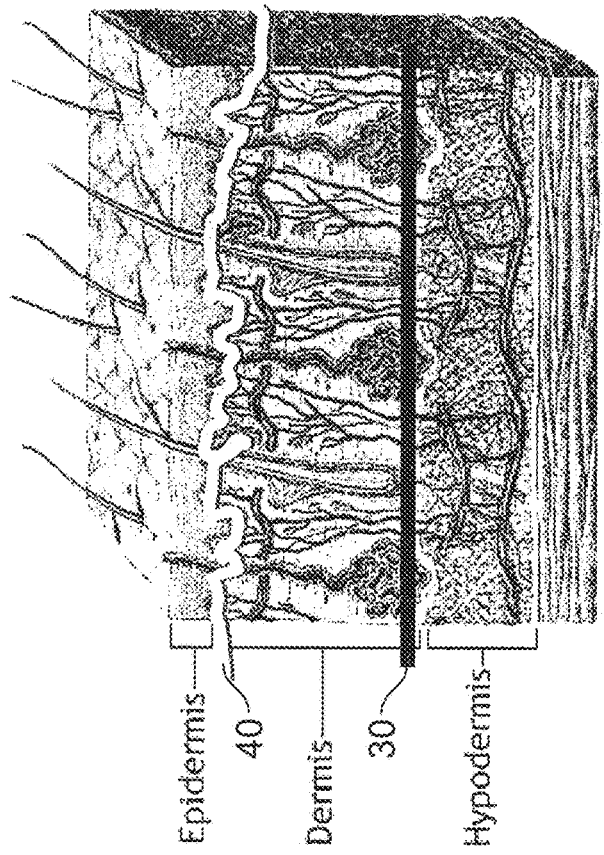
FIG. 5a is a perspective schematic view of a prior art process, as performed on a section of human skin.

FIG. 5a illustrates the process for fabricating the prior art ACDMs (i.e., the FlexHD® Structural™ ACDM, AlloDerm® ACDM and AlloDerm® RTU ACDM), namely, cutting the lower portion of the dermis and hypodermis (represented by straight line 30), and chemically treating the tissue to remove only the epidermis (represented by uneven line 40) and expose the DEJ.

FIG. 5b illustrates the process for fabricating the Disclosed ACDM according to an embodiment of the present invention. The lower portion of the dermis and hypodermis are cut (represented by straight line 50), and then a second cut (represented by straight line 60), is made deeper into the dermis than the chemical treatment used to fabricate the prior art ACDMs. In one embodiment, the second cut results in the removal of the epidermis, the DEJ, and the upper, epidermal portion of the papillary dermis.

Presented and discussed below are Examples that illustrate the comparative biomechanical properties of the Disclosed ACDM and the prior art ACDMs (i.e., the FlexHD® Structural™ ACDM, AlloDerm® ACDM and AlloDerm® RTU ACDM).

Example 1—In Vitro Fibroblast Attachment to the ACDMs

Materials and Methods 7 mm punches of each tissue sample (i.e., each ACDM) were prepared and seeded with $1 \times 10^5$ BJ neonatal human foreskin fibroblasts (ATCC, Manassa, Va.) on both sides in Eagles Minimum Essential Medium+10% fetal bovine serum. After 30 minutes, the tissue sections were washed to remove any non-adherent cells and incubated at 37° C. for 1 hour in complete growth medium. Attached cells were quantified using CyQuant Cell Proliferation Assay (Invitrogen, Carlsbad, Calif.) according to the manufacturer's instructions. Non-adherent seeded controls were measured for all samples. The test was replicated with each sample set. Values for cell fluorescence were reported. Tissue from multiple donor lots were collected, processed as described and tested. In addition, five lots of AlloDerm® RTU thick tissue were obtained and tested as commercial controls.

Results

TABLE 1

In vitro fibroblast attachment

|  | No. of Samples | Cells* | Grouping** |
|---|---|---|---|
| FlexHD Structural |  |  |  |
| Dermis | 60 | 6047/242 | BC |
| Epidermis | 60 | 2620/270 | D |
| Disclosed ACDM |  |  |  |
| Dermis | 77 | 8379/308 | A |
| Epidermis | 78 | 7246/359 | AB |
| AlloDerm |  |  |  |
| Dermis | 42 | 4568/476 | C |
| Epidermis | 42 | 1548/379 | DE |
| AlloDerm RTU |  |  |  |
| Dermis | 36 | 2028/259 | DE |
| Epidermis | 36 | 1039/278 | E |

*Data presented as fluorescence units: mean/standard error of the mean, SEM.
**Statistically similar groups as determined by the Bonferroni Method (95% Confidence); means that do not share a letter are statistically different.

Figure 6:
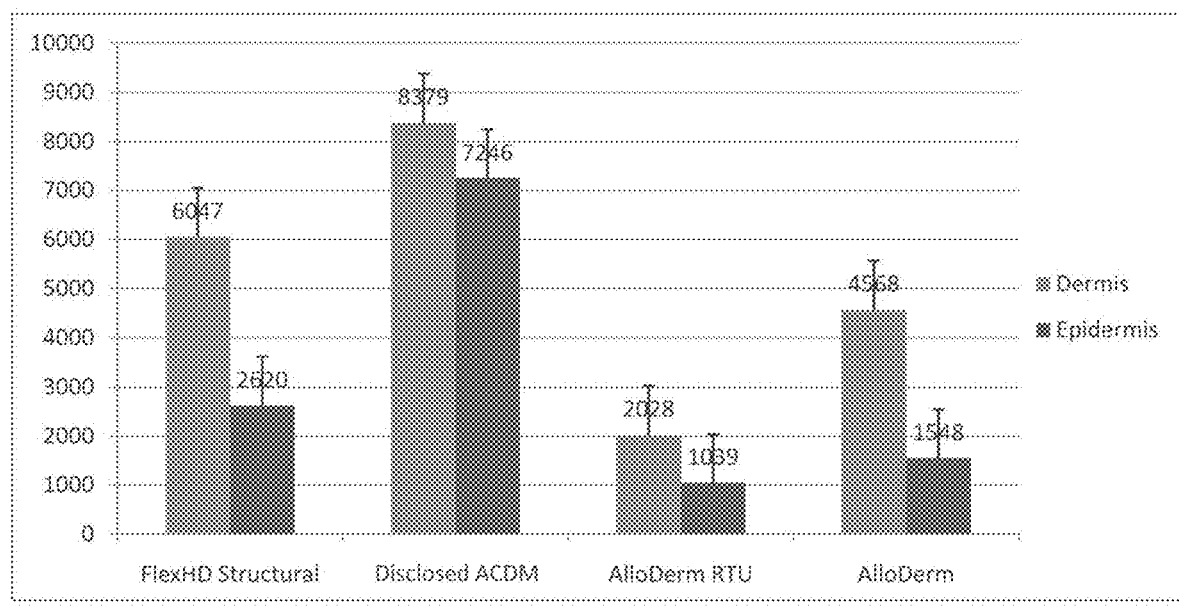
FIG. 6 is a graph of in vitro fibroblast attachment data for various ACDMs.

The results presented above are organized to show fibroblast attachment data for the dermis side and, separately, the epidermis side of each of the ACDMs. These results are similarly organized in the graph of FIG. 6 and the following discussion.

Dermal Side of Tissue:

The Disclosed ACDM had a statistically significant higher number of attached fibroblasts as compared to the FlexHD Structural ACDM; 8379 vs. 6047 fluorescence units. The AlloDerm ACDM had a greater number of attached fibroblasts as compared to the AlloDerm RTU ACDM; 4568 vs. 2028. It is noteworthy that the AlloDerm RTU ACDM had less than half as many attached fibroblasts as compared to the AlloDerm ACDM; this is a statistically significant difference. Finally, the number of attached fibroblasts for the Disclosed ACDM (8379) was much greater than for either the AlloDerm ACDM (4568) or AlloDerm RTU ACDM (2028). These differences are also statistically significant.

Epidermal Side of Tissue:

The Disclosed ACDM had a statistically significant higher number of attached fibroblasts as compared to the FlexHD Structural ACDM; 7246 vs. 2620 fluorescence units. The AlloDerm ACDM had roughly the same level of attached fibroblasts as the AlloDerm RTU ACDM; 1548 vs. 1039. These were much lower than for the FlexHD Structural ACDM or the Disclosed ACDM. Accordingly, the Disclosed ACDM had a much higher level of attached fibroblasts (7246) as compared to either the AlloDerm ACDM (1548) or the AlloDerm RTU ACDM (1039). The difference between the cell attachment level for the Disclosed ACDM is statistically significantly different than for either of the AlloDerm ACDM or the AlloDerm RTU ACDM.

Discussion

The Disclosed ACDM is derived from a deeper cut into the dermis layer relative to the source of the FlexHD Structural ACDM (see, e.g., FIGS. 5a and 5b). The porosity of this tissue increases with increased depth into the dermis. Accordingly, the interconnected channels are larger. As a corollary, the pores are more uniform at the two surfaces of a deep cut dermis.

In Table 1, the data show that the deeper cut Disclosed ACDM has many more attached fibroblasts than the FlexHD Structural ACDM. Also, the in vitro fibroblast attachment is clearly different for the two sides, dermis and epidermis, of the FlexHD Structural ACDM. For the deeper cut Disclosed ACDM, the in vitro fibroblast attachment is more equal for the two sides. Both the AlloDerm and AlloDerm RTU ACDMs have much lower numbers of attached fibroblasts than do either the Disclosed ACDM or the FlexHD Structural ACDM. The Disclosed ACDM actually has a 76% higher frequency of fibroblast attachment compared to that of the AlloDerm RTU ACDM. The AlloDerm RTU ACDM has a 56% lower frequency of cell attachment than that of the AlloDerm ACDM.

Example 2—Tensile Properties of the ACDMs

Materials and Methods

Tissue samples (i.e., for each ACDM) were tested on an MTS 858 Mini Bionix System. Sample thickness was first measured with a laser micrometer (Z Mike, Benchmike 4050S). Samples in dogbone configuration (1 cm×7 cm; ASTM 638) were positioned in pneumatic action grips set at 29 psi pressure at a gage length of 26 mm. Tissue was pulled to break at a strain rate of 50.6 mm/min. Ultimate tensile strength, elongation-at-break and elastic modulus were recorded. Statistical analysis included both tests of the means and the estimates of variability for tensile strength, elongation-at-break, and modulus.

Results

As a result of the more open structure and greater porosity of the Disclosed ACDM, as contrasted with the FlexHD Structural ACDM, the Disclosed ACDM has reduced tensile strength as compared to the FlexHD Structural ACDM; 10.97 vs. 15.36 MPa.

Figure 7:
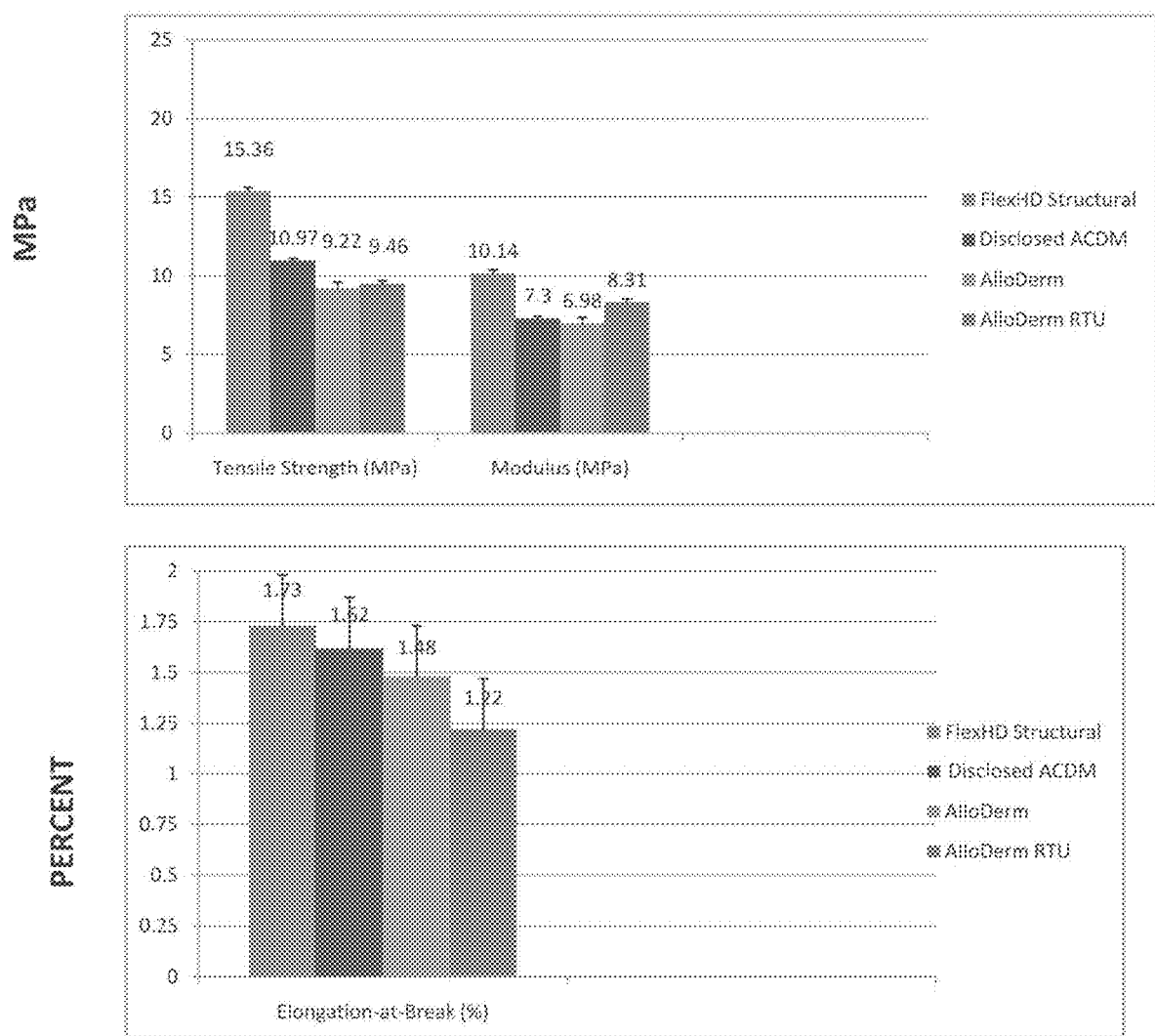
FIG. 7 is a group of graphs of tensile property data for various ACDMs.

As can be seen from the data in Table 2 and the graph illustrated in FIG. 7, the Disclosed ACDM had a tensile strength higher than that of both the AlloDerm and AlloDerm RTU ACDMs; (10.97 vs. 9.22 and 9.46 MPa, respectively). These differences are statistically significant.

Modulus is a measure of flexibility. In other words, the greater its modulus, the more stiffness a material exhibits. The modulus of the Disclosed ACDM was 38% lower (and therefore less stiff) than that of the FlexHD Structural ACDM; 7.30 vs. 10.14 MPa (see the graph illustrated in FIG. 7). This difference is statistically significant.

The modulus of the Disclosed ACDM is statistically equivalent to that of the AlloDerm ACDM; 7.30 vs. 6.98 MPa (see the graph illustrated in FIG. 7). The AlloDerm RTU ACDM was, however, less flexible than either the AlloDerm ACDM or the Disclosed ACDM; 8.31 vs. 6.98 or 7.30 MPa. These differences are statistically significant. Based on the modulus results, the AlloDerm RTU ACDM was 19% stiffer than the AlloDerm ACDM. This difference is statistically significant.

Elongation-at-break is a measure of the amount of stretch before tensile failure. For this parameter, the Disclosed ACDM and the AlloDerm ACDM were statistically equivalent; 1.73 vs. 1.62 mm/mm. The AlloDerm RTU ACDM, however, had a statistically lower elongation-at-break as compared to either the Disclosed ACDM or the AlloDerm ACDM; 1.22 mm/mm vs. 1.73 or 1.48 mm/mm.

Example 3—Surface Characterization of the ACDMs by Scanning Electron Microscopy (SEM)

Materials and Methods

Tissue samples (i.e., for the Disclosed ACDM and the FlexHD Structural ACDM) were lyophilized and coated with a 10 nm layer of gold. Images were taken using a Field Emission Zeiss Scanning Microscope (Carl Zeiss, Inc., Thornwood, N.Y.) with a working distance of 5-10 mm and voltage range of 30-200 kV. All images were taken at the Department of Ceramics and Material Science at Rutgers University, New Brunswick, N.J.

Results

Figure 8A:
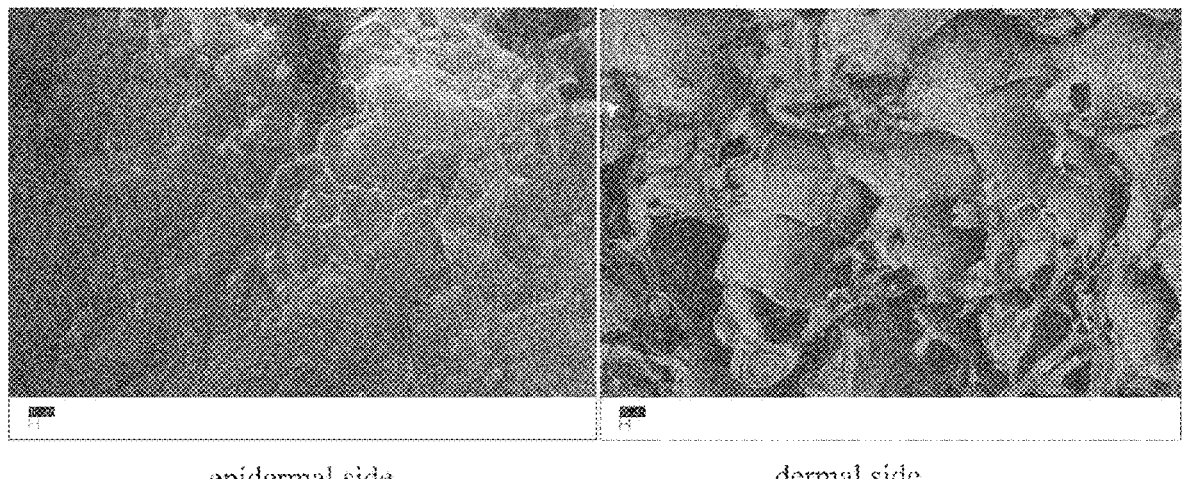
FIGS. 8a and 8b are scanning electron micrographs of various ACDMs.
Figure 8B:
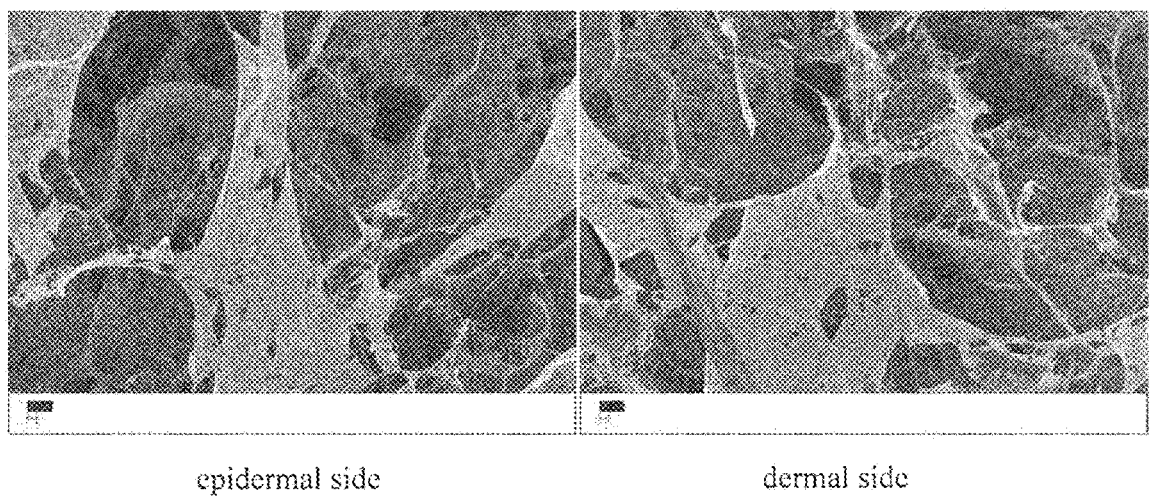

Scanning electron micrographs of the epidermal side and the dermal side of both the FlexHD Structural ACDM and the Disclosed ACDM are presented in FIGS. 8a and 8b, respectively. Representative images were taken at 250× for all samples. For both ACDMs, the micrographs of the epidermal side of the ACDMs are shown on the left, and the micrographs of the dermal side are shown on the right.

Discussion

The deeper cut method of the present invention that was used to derive the Disclosed ACDM results in a different

TABLE 2

TENSILE PROPERTIES*
DERMAL TISSUES FOR PLASTIC SURGERY

| TISSUE | NO. OF DONORS | NO. OF SAMPLES | ULTIMATE TENSILE STRENGTH mean/SEM (MPa) | Grouping** | MODULUS mean/SEM (MPa) | Grouping | ELONGATION-AT-BREAK mean/SEM (%) | Grouping |
|---|---|---|---|---|---|---|---|---|
| Flex HD Structural Disclosed | 5 | 154 | 15.36/0.34 | A | 10.14/0.25 | A | 1.73/0.04 | A |
| ACDM | 6 | 300 | 10.97/0.21 | B | 7.30/0.13 | C | 1.62/0.02 | AB |
| Alloderm | 11 | 88 | 9.22/0.54 | C | 6.98/0.38 | C | 1.48/0.05 | B |
| Alloderm RTU | 6 | 100 | 9.46/0.22 | C | 8.31/0.22 | B | 1.22/0.02 | C |

*Data presented as mean/standard error of the mean, SEM.
**Statistically similar groups as determined by the Bonferroni Method (95% Confidence); means that do not share a letter are statistically different.

Discussion

Since the porosity of the tissue in the Disclosed ACDM is significantly greater than that of the FlexHD Structural ACDM, the tensile properties were expected to be different; this difference was confirmed. The Modulus, a measure of flexibility, was 38% lower, i.e., more flexible for the deeper cut Disclosed ACDM relative to the FlexHD Structural ACDM. Also, the Disclosed ACDM had a higher level of flexibility (13.8%) relative to the AlloDerm RTU ACDM.

The stretchability of these tissues may be expressed in terms of the elongation-at-break data. The stretchability of the Disclosed ACDM and the AlloDerm ACDM were equivalent. However, the stretchability of the Disclosed ACDM by this measure is 33% higher relative to the AlloDerm RTU ACDM.

An expected decrease in tensile strength of 29% was observed in the Disclosed ACDM, relative to that of the FlexHD Structural ACDM. It is noteworthy that the tensile strength of the Disclosed ACDM was 40% greater than for the AlloDerm ACDM and 39% greater than for the AlloDerm RTU ACDM.

microstructure as compared to that of the FlexHD Structural ACDM. In contrast to the FlexHD Structural ACDM, the SEM images clearly show the more open and porous structure of the Disclosed ACDM. The dermal and epidermal sides are very similar for the Disclosed ACDM.

Example 4—Surface Appearance of the ACDMs by Histology (Hematoxylin & Eosin Staining)

Materials and Methods

Tissue sections (i.e., for the Disclosed ACDM and the FlexHD Structural ACDM) were fixed in 10% neutral buffered formalin prior to paraffin embedding, sectioned and stained via hematoxillin and eosin (H & E). All histological processing was performed at Premier Laboratory (Longmont, Colo.). Imaging was also performed at Premier using AperioScope software (Vista, Calif.). Representative images were taken at 10× magnifications.

Results

Figure 9A:
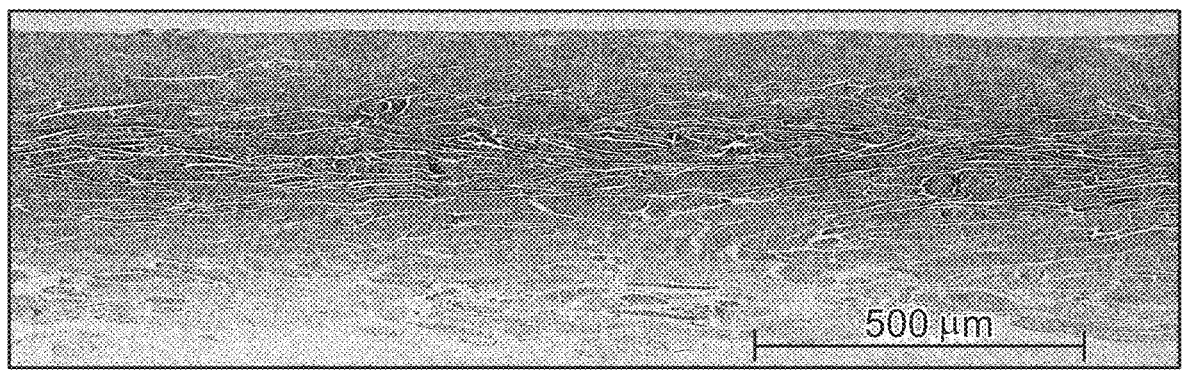
FIGS. 9a and 9b are histological images of various ACDMs.
Figure 9B:
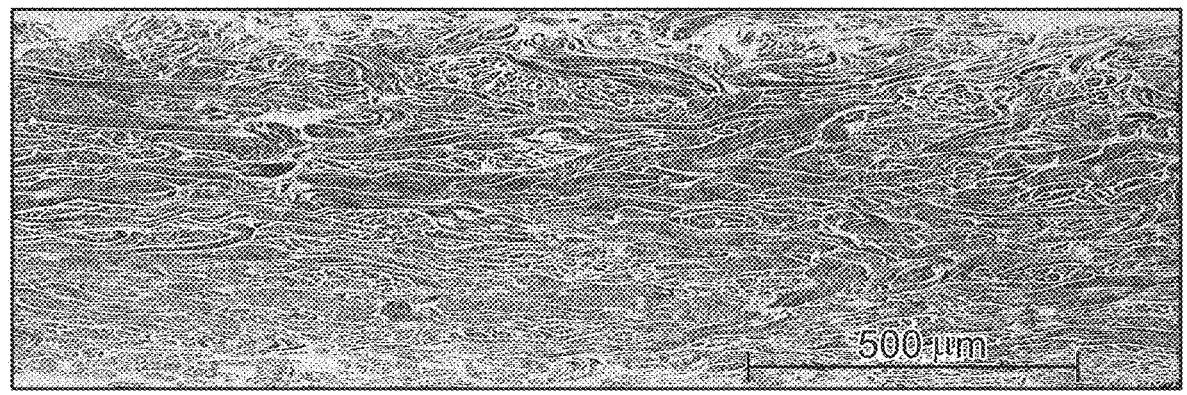

Images of the stained FlexHD Structural ACDM and the Disclosed ACDM are presented in FIGS. 9a and 9b, respectively. The images are low magnification (10×) representative scans of the entire thickness of the tissue samples. In all images, the epidermal side is on the upper part of the scan.

However, it should be noted that orientation for these samples was not maintained throughout histological processing. In some cases, the samples are virtually symmetrical through the thickness and when possible, macrostructural landmarks (such as presence of adipose or hair follicles) were used to identify sidedness.

As expected and illustrated in FIG. 9a, the FlexHD Structural ACDM shows a dense structure with an even topography on the epidermal side. Towards the dermal side, the structure becomes less dense, with the tissue directly adjacent to the cut edge showing high fragmentation. On the other hand, FIG. 9b shows that the Disclosed ACDM possesses a more uniform collagen matrix with no distinguishable differences between the epidermal and dermal sides.

Discussion

The histology images are consistent with the SEM images of FIGS. 8a and 8b, showing the similarity of the dermal and epidermal sides of the Disclosed ACDM. Based on the results in Examples 3 and 4, the Disclosed ACDM will cause relatively less confusion and concern about identifying and maintaining the side orientation thereof, when compared to FlexHD Structural ACDM and other ACDMs.

Example 5—Suture Retention Strength Testing of the ACDMs

Materials and Methods

A size 0 PDS® II suture with a 40 mm, ½ circle tapered needle (Ethicon, Inc., Somerville, N.J.) was placed 5 mm from the edge of 6 cm×1 cm test samples of the Disclosed ACDM, the FlexHD Structural ACDM and the AlloDerm ACDM. With one end of the sample fixed, the suture was pulled through the material of the sample until failure. The load at failure was recorded on a MTS Mini Bionix System.

Results

TABLE 3

Suture Retention*

| ACDM Sample | No. of Donors | No. of Samples | Suture Retention Strength (MPa) Mean/SEM | Grouping** |
|---|---|---|---|---|
| FlexHD Stuctural ACDM | 40 | 709 | 3.40/0.03 | B |
| Disclosed ACDM | 9 | 214 | 4.10/0.07 | A |
| AlloDerm ACDM | 10 | 121 | 3.20/0.9 | B |

*Data presented as mean/standard error of the mean, SEM.
**Statistically, similar groups as determined by the Bonferroni Method (95% Confidence); means that do not share a letter are statistically different.

Figure 10:
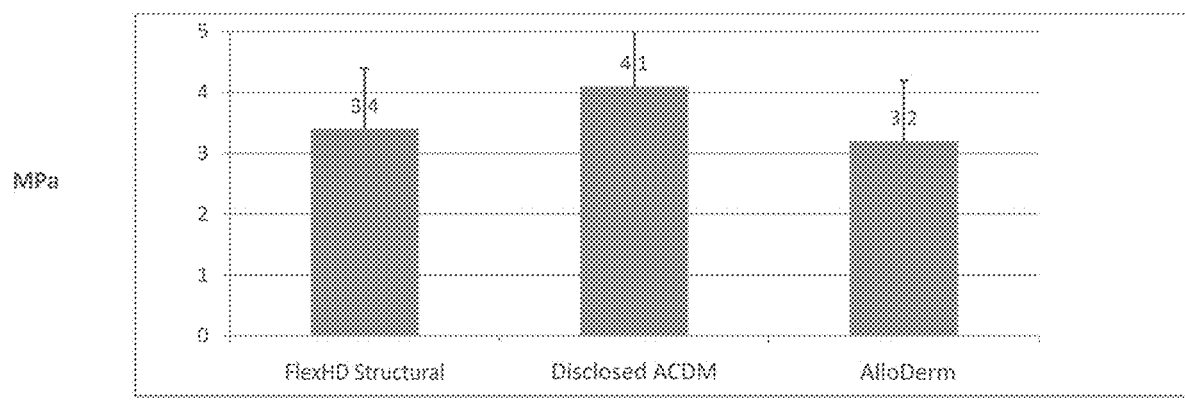
FIG. 10 is a graph of suture retention strength data for various ACDMs.

The ability of the Disclosed ACDM to be sutured without tearing (i.e., its suture retention strength) is statistically significantly higher than that for the AlloDerm ACDM and the FlexHD Structural ACDM (4.1 vs. 3.2 MPa and 4.1 vs. 3.4 MPa, respectively). The suture retention strengths of the AlloDerm ACDM and the FlexHD Structural ACDM were similar, and equivalent statistically. These results also presented in the graph of FIG. 10 and further discussed below.

Discussion

The ability of the Disclosed ACDM to resist tearing under load applied to the suture demonstrates that the Disclosed ACDM has somewhat higher suture pull-out values than that of the FlexHD Structural and AlloDerm ACDMs.

The higher suture retention strength of the Disclosed ACDM may be attributed to its increased flexibility arising from its more open, porous structure. The resilience provided by this "open net" structure could account for the higher suture retention strength.

Example 6—Variability of Tensile Properties of the ACDMs

Materials and Methods

A comparison of the variability of tensile properties was made between the Disclosed ACDM and the AlloDerm ACDM.

Statistical analyses were made of the standard deviations of the means for each tensile parameter: Ultimate tensile strength, Modulus, and Elongation-at-break. The standard deviations were compared using two independent statistical methods, F-test and Levine's test.

Statistical differences in the variability of the mean is established by two independent statistical methods. The standard F-Test demonstrates a very high statistically different level of variability in the tensile data with a p-value of 0.000. In addition, as a test for data with non-uniform distribution, the Levine test again demonstrates differences in the data variability at a statistically significant level with a p-value of 0.016.

Results

Figure 11A:
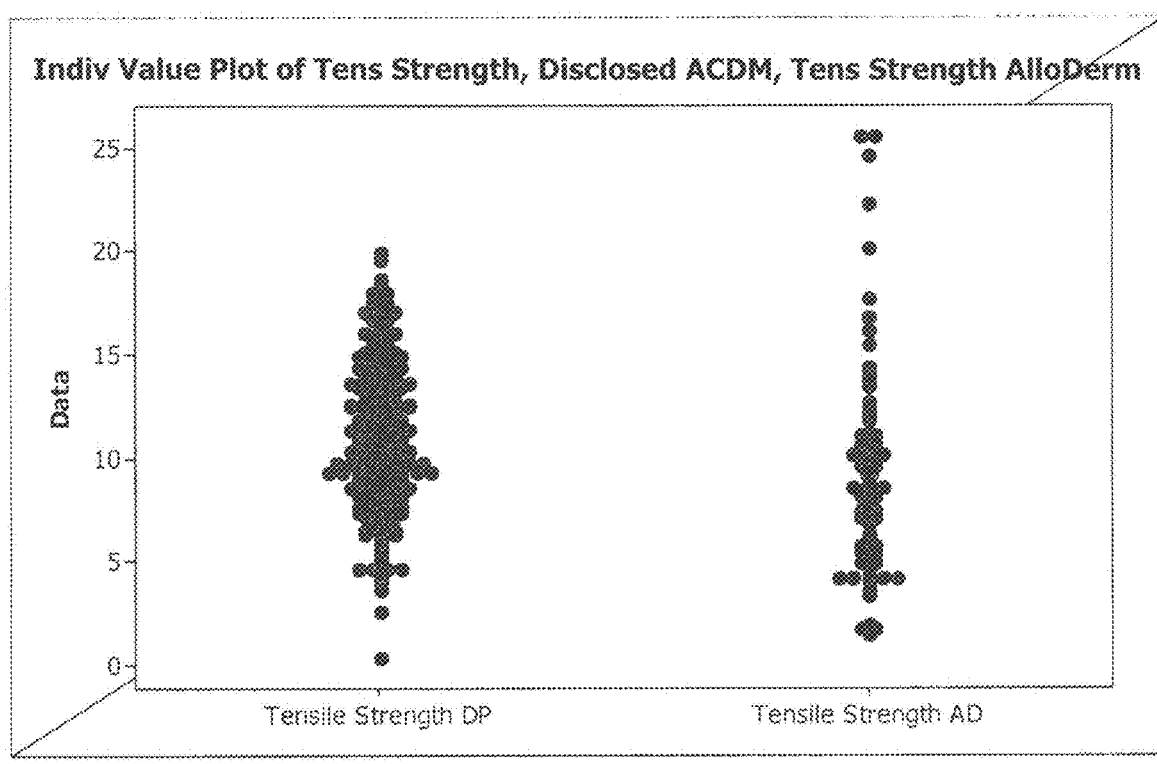
FIG. 11a is a plot of standard deviations in the tensile strength data for various ACDMs.
Figure 11B:
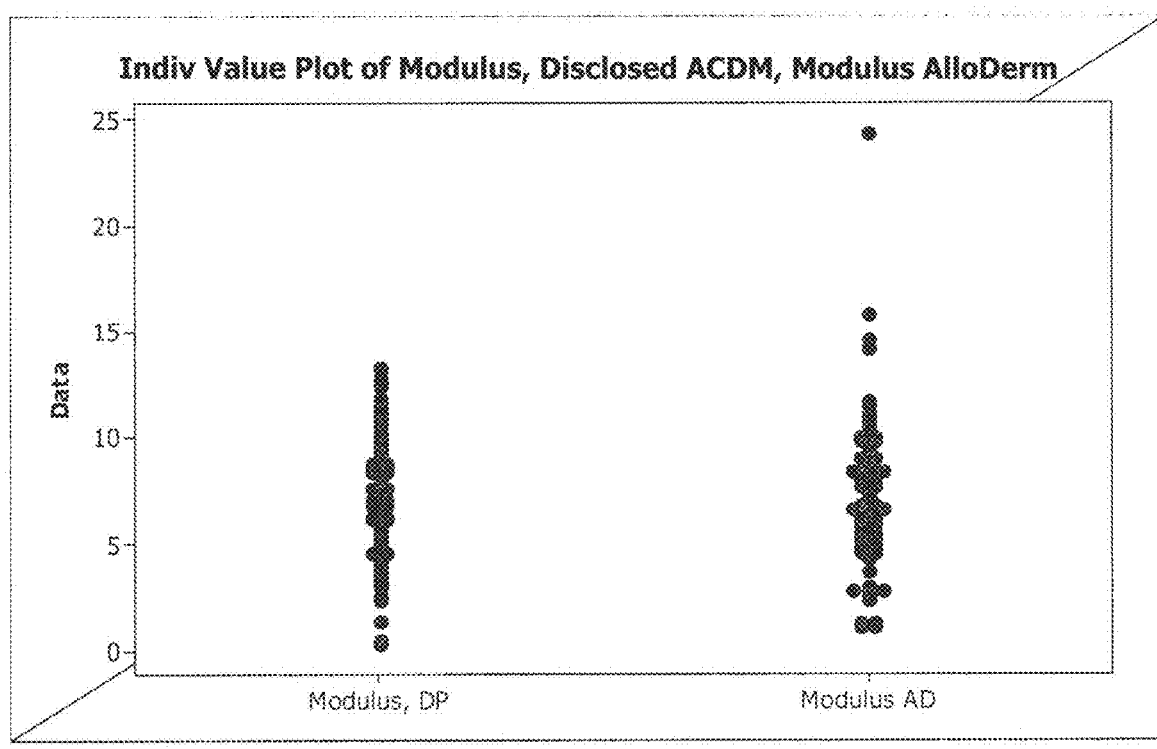
FIG. 11b is a plot of standard deviations in the modulus data for various ACDMs.
Figure 11C:
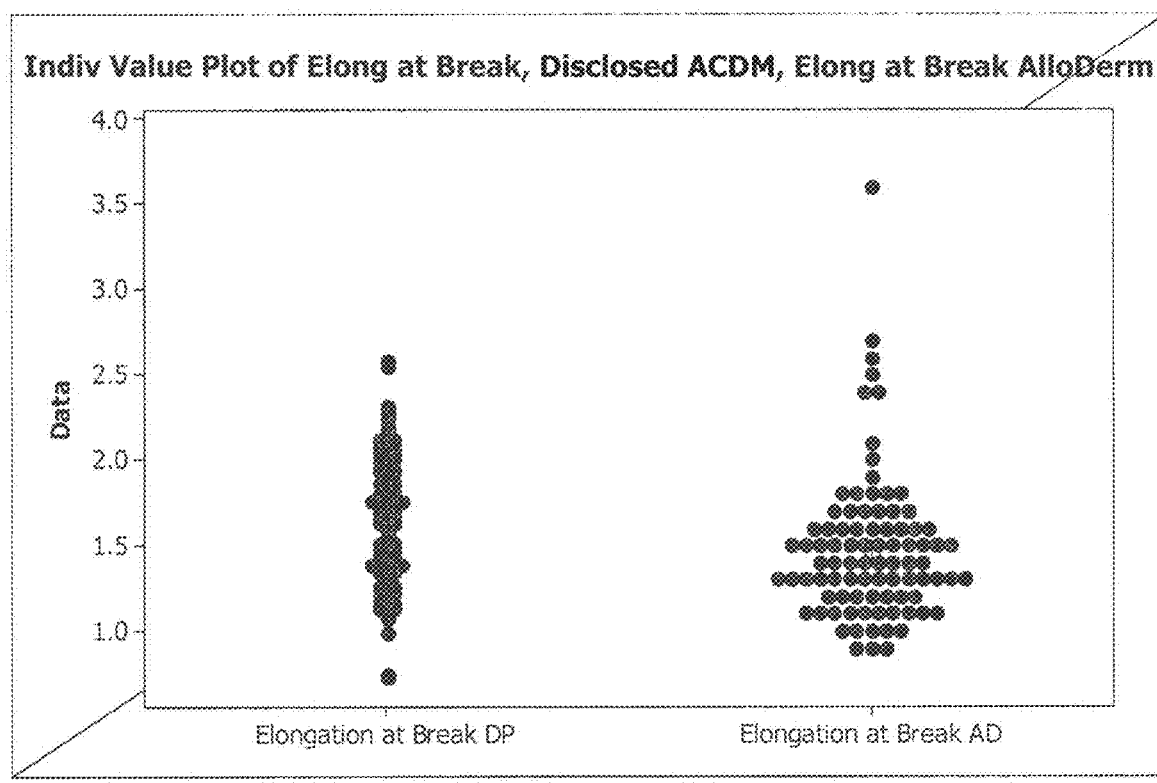
FIG. 11c is a plot of standard deviations in the elongation-at-break data for various ACDMs.

The data and results of the statistical analyses are presented in Table 4 and FIGS. 11a, 11b and 11c.

For Ultimate Tensile Strength (see FIG. 11a), the standard deviation for the Disclosed ACDM ("DP", left side) was statistically significantly lower than that of the AlloDerm ACDM ("AD", right side); 3.557 vs. 5.076. The statistical difference was valid for both statistical methods used.

For Modulus (see FIG. 11b), the standard deviation for the Disclosed ACDM ("DP", left side) was statistically significantly lower than that of the AlloDerm ACDM ("AD", right side); 2.260 vs. 3.532. The statistical difference was valid for both statistical methods used.

For Elongation-at-break (see FIG. 11c), the standard deviation of the Disclosed ACDM ("DP", left side) was statistically significantly lower than that of the AlloDerm ACDM ("AD", right side); 0.33 vs. 0.43. The statistical difference was valid utilizing the F-test.

The more uniform tensile properties of the Disclosed ACDM relative to those of the AlloDerm ACDM can readily be seen in the plots of individual values for the three tensile parameters, as shown in FIGS. 11a, 11b and 11c.

TABLE 4

VARIABILITY OF TENSILE PROPERTIES

| | Tensile Strength | | Modulus | | Elongation-at-Break | |
|---|---|---|---|---|---|---|
| | Disclosed ACDM | Alloderm | Disclosed ACDM | Alloderm | Disclosed ACDM | Alloderm |
| Standard Deviation | 3.557 | 5.076 | 2.260 | 3.532 | 0.334 | 0.434 |
| Sample Size # Donors/ # Samples | 5/300 | 11/87 | 5/300 | 11/87 | 5/300 | 11/88 |

TABLE 4-continued

VARIABILITY OF TENSILE PROPERTIES

| | Tensile Strength | | Modulus | | Elongation-at-Break | |
|---|---|---|---|---|---|---|
| | Disclosed ACDM | Alloderm | Disclosed ACDM | Alloderm | Disclosed ACDM | Alloderm |
| Statistically Significant | | | | | | |
| F-Test | YES | | YES | | YES | |
| Levine's Test | YES | | YES | | NO* | |

*Data for Alloderm Elongation-At-Break is abnormally distributed.

Discussion

Variability of the tensile properties is much less for the Disclosed ACDM as compared to the Alloderm ACDM. While there appears to be a small difference in the actual tensile properties between the Disclosed ACDM and the AlloDerm ACDM there is, however, a very significant difference in the variability of the tensile properties for these two dermal matrices. For all three tensile properties measured (i.e., tensile strength, modulus and elongation-to-break), the Disclosed ACDM exhibits a statistically lower variability of the tensile values than the AlloDerm ACDM. This results in greatly improved uniformity of handling properties among individual pieces. Consequently, the Disclosed ACDM is a more predictable tissue form.

To summarize the findings of the above Examples, the process for forming the Disclosed ACDM minimizes foreign body reactions while promoting vascularization, cellular attachment, and tissue ingrowth. The Disclosed ACDM becomes well incorporated into the surrounding tissues while avoiding adhesions. Tensile properties (strength, pliability and handling characteristics) of the Disclosed ACDM are optimized. Suture retention strength and uniformity of tensile properties are also significantly improved for the Disclosed ACDM. The Disclosed ACDM is very strong and closely mimic the biomechanical properties of the tissue that it is intended to replace. The Disclose ACDM maintains an optimal elasticity and deformability suited for the intended use, e.g., as a sling for use with breast implants and/or tissue expanders in breast reconstruction surgery.

Another allograft tissue form may be simultaneously derived using the process disclosed above in connection with the Disclosed ACDM. More particularly, an allograft tissue form is derived by the first cut made 10 into the reticular dermis RD of the skin to remove the underlying hypodermis H, as discussed above and illustrated in FIG. 2. The cut portion of the reticular dermis RD remains attached to the underlying hypodermis H, and therefore constitutes a "hybrid bilayer" tissue form that includes both a dermal side and an adipose (i.e., fat) tissue side. Such a tissue form is useful in surgical procedures in which both dermis and adipose tissue are required or desired, as the two tissues may serve different functions (e.g., a repair function and a bulking function, respectively). One example of such a surgical procedure is breast reconstructive surgery. Other examples may include various plastic, cosmetic and/or reconstructive surgeries.

It will be understood that the embodiments described herein are merely exemplary and that a person of ordinary skill in the art may make many variations and modifications without departing from the spirit and scope of the invention. All such variations and modifications are intended to be included within the scope of the invention, and the appended claims. Some of the possible variations and modifications of the Disclosed ACDM and the dermis/adipose hybrid bilayer tissue form are disclosed below.

The Disclosed ACDM may be provided in particulated form in one embodiment, depending on the intended surgical use. The dermis/adipose hybrid bilayer tissue form may also be provided in particulated form in one embodiment. In other embodiments, the particulated Disclosed ACDM and/or particulated dermis/adipose bilayer hybrid tissue form may be combined with a carrier, and thereby constitute a flowable tissue form.

In other embodiments, the Disclosed ACDM may be provided in perforated or meshed form. Perforating the Disclosed ACDM or forming a mesh of the Disclosed ACDM makes it more porous, and ideal for certain surgical applications. The dermis/adipose hybrid bilayer tissue form may also be provided in perforated or meshed form in other embodiments.

In other embodiments, cells may be added to the Disclosed ACDM. Cells may also be added to the dermis/adipose hybrid bilayer tissue form. Such cells may include, for example, stem cells (e.g., embryonic stem cells, mesenchymal stem cells, adult stem cells, skin-derived stem cells, and amnion-derived stem cells), fibroblasts, osteoblasts, myoblasts, and keratinocytes.

In other embodiments, biological substances may be added to the Disclosed ACDM. Biological substances may also be added to the dermis/adipose hybrid bilayer tissue form. Such biological substances may include, for example, platelet-rich plasma ("PRP"), bone marrow aspirate, and/or demineralized bone particles or fibers and/or other allograft tissue forms. Further, amnion tissue (with or without the native cells thereof) may be added to the Disclosed ACDM and/or the dermis/adipose hybrid bilayer tissue form, e.g., to function as an anti-adhesion membrane.

In other embodiments, the Disclosed ACDM may be used to wrap around the above-identified biological substances or other biological substances. In such a wrapper function, the Disclosed ACDM may protect, enclose, and or insulate such biological substances upon implantation. The dermis/adipose hybrid bilayer tissue form may also be used as a wrapper for biological substances.

In other embodiments, reinforcing elements may be added to the Disclosed ACDM. Reinforcing elements may also be added to the dermis/adipose bilayer tissue form. Examples of such reinforcing elements include absorbable fibers and non-absorbable fibers. The reinforcing elements may be arranged in various patterns, such as, for example, a grid pattern.

In other embodiments, the Disclosed ACDM may be chemically modified to imbue it with enhanced properties. One example is cross-linking the collagen of the Disclosed ACDM. The dermis/adipose hybrid bilayer tissue form may also be chemically modified.

In other embodiments, the tissue resulting from the above-described process, in which the epidermis, the dermis-epidermis junction and the epidermal portion of the papillary dermis are removed from the dermal portion of the papillary dermis and the reticular dermis, may be processed such that it is suitable for use in surgical breast procedures. In such embodiments, as for the Disclosed ACDM, the tissue (i.e., the reticular dermis and the dermal portion of the papillary dermis that remain after the epidermis, the dermis-epidermis junction and the epidermal portion of the papillary dermis have been removed) is decellularized by chemically treating it with saline, detergent, peracetic acid, ethanol and propylene glycol. The tissue is then washed with sterile water to remove residual processing chemicals. In an embodiment, the disinfected and acellular tissue is cut into grafts having a contoured profile such that they are suitable for clinical uses. The grafts are treated with aqueous ethanol and then packaged to provide a hydrated collagen matrix.

Figure 12:
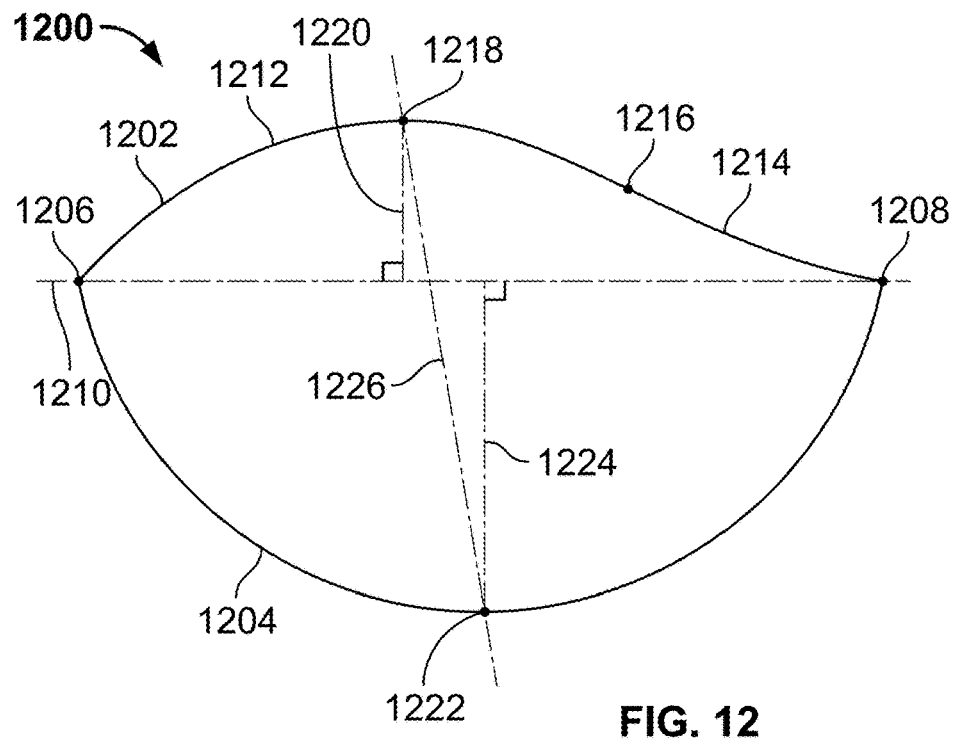
FIG. 12 is a top plan view of a first embodiment of an ACDM as adapted for use in breast reconstruction surgery.

In an embodiment, the contoured profile is selected such that the resulting graft is adapted for use in a surgical breast procedure. FIG. 12 is a top plan view of an exemplary asymmetric tissue graft 1200 suitable for use in surgical breast procedures. The asymmetric tissue graft 1200 includes a first peripheral edge 1202 and a second peripheral edge 1204. The first peripheral edge 1202 and second peripheral edge 1204 meet at a first vertex 1206 and a second vertex 1208. A first imaginary axis 1210 extends between the first vertex 1206 and the second vertex 1208. The first imaginary axis 1210 is an imaginary element defined herein for the purpose of describing the structure of the asymmetric tissue graft 1200, and it therefore is not a physical feature of the asymmetric tissue graft 1200.

Continuing to refer to FIG. 12, the first peripheral edge 1202 includes a convex portion 1212, which is convex with respect to (i.e., curves away from) the first imaginary axis 1210, and a concave portion 1214, which is concave with respect to (i.e., curves toward) the first imaginary axis 1210. A transition point 1216 is located at the location where the convex portion 1212 of the first peripheral edge 1202 meets the concave portion 1214 of the first peripheral edge 1202. The second peripheral edge 1204 is convex, along its entire length, with respect to (i.e., curves away from) the first imaginary axis 1210.

Continuing to refer to FIG. 12, the first peripheral axis 1202 includes an apogee 1218. As used herein, an apogee is the point along the length of the first peripheral edge 1202 that is furthest from the first imaginary axis 1210, as measured along a perpendicular imaginary segment 1220 extending from the apogee 1218 and perpendicular to the first imaginary axis 1210, of any point along the first peripheral edge 1202. In other words, the segment 1220 corresponding to the apogee 1218 is longer than any of the other imaginary segments extending from every other point along the first peripheral edge 1202 to the first imaginary axis 1210 in a direction perpendicular to the first imaginary axis 1210. The apogee 1218 is located at a point along the length of the convex portion 1212 of the first peripheral edge 1202.

Continuing to refer to FIG. 12, the second peripheral edge 1204 includes an apogee 1222. An imaginary segment 1224 extends from the apogee 1222 to the first imaginary axis 1210 in a direction perpendicular to the first imaginary axis 1210, and is longer than any of the other imaginary segments extending from every other point along the second peripheral edge 1204 to the first imaginary axis 1210 in a direction perpendicular to the first imaginary axis 1210. A second imaginary axis 1226 extends through the apogee 1218 and the apogee 1222. The second imaginary axis 1226 is not perpendicular to the first imaginary axis 1210.

Figure 13:
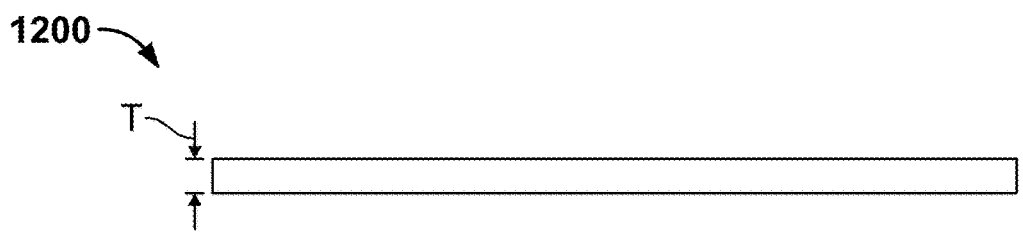
FIG. 13 is a front elevational view of the ACDM of FIG. 12.

FIG. 13 is a front plan view of the exemplary asymmetric tissue graft 1200. The asymmetric tissue graft 1200 has a thickness (T) that is substantially uniform over the entire profile of the asymmetric tissue graft 1200 as shown in FIG. 12. In an embodiment, the thickness (T) is in a range between 0.5 mm and 3.0 mm. In an embodiment, the asymmetric tissue graft 1200 may be provided in "thick" and "thin" versions. In an embodiment, for a "thick" version of the asymmetric tissue graft 1200, the thickness (T) may be in a range between 1.5 mm and 2.5 mm. In an embodiment, for a "thin" version of the asymmetric tissue graft 1200, the thickness (T) may be in a range between 0.6 mm and 1.4 mm. In an embodiment, the asymmetric tissue graft 1200 may be provided in a variety of sizes such that a surgeon performing a surgical breast procedure may choose an asymmetric tissue graft 1200 that is optimally sized for the patient, and correspondingly, does not need to cut a graft to size during a surgical procedure. In an embodiment, an appropriately sized asymmetric tissue graft 1200 may be selected based on the volume of an implant (e.g., a saline implant) to be supported by the asymmetric tissue graft 1200.

In an embodiment, the asymmetric tissue graft 1200 includes a width of 15 cm as measured from the first vertex 1206 to the second vertex 1208, a first portion height of 30 mm as measured along the imaginary segment 1220, and a second portion height of 60 mm as measured along the imaginary segment 1224. In an embodiment, the asymmetric tissue graft 1200 includes a width of 19 cm as measured from the first vertex 1206 to the second vertex 1208, a first portion height of 37 mm as measured along the imaginary segment 1220, and a second portion height of 63 mm as measured along the imaginary segment 1224. In an embodiment, the asymmetric tissue graft 1200 includes a width of 20 cm as measured from the first vertex 1206 to the second vertex 1208, a first portion height of 40 mm as measured along the imaginary segment 1220, and a second portion height of 70 mm as measured along the imaginary segment 1224. In an embodiment, the asymmetric tissue graft 1200 includes a width of 22 cm as measured from the first vertex 1206 to the second vertex 1208, a first portion height of 50 mm as measured along the imaginary segment 1220, and a second portion height of 80 mm as measured along the imaginary segment 1224. In an embodiment, the asymmetric tissue graft 1200 includes a width of 24 cm as measured from the first vertex 1206 to the second vertex 1208, a first portion height of 55 mm as measured along the imaginary segment 1220, and a second portion height of 95 mm as measured along the imaginary segment 1224.

In an embodiment, a ratio of the second portion height, as measured along the imaginary segment 1224, to the first portion height, as measured along the imaginary segment 1220, is in a range of from about 1.5 to about 2.0. In an embodiment, a ratio of the width, as measured from the first vertex 1206 to the second vertex 1208, to the first portion height, as measured along the imaginary segment 1220, is in a range of from about 4.2 to about 5.3. In an embodiment, a ratio of the width, as measured from the first vertex 1206 to the second vertex 1208, to the second portion height, as measured along the imaginary segment 1224, is in a range of from about 2.4 to about 3.1.

Figure 14:
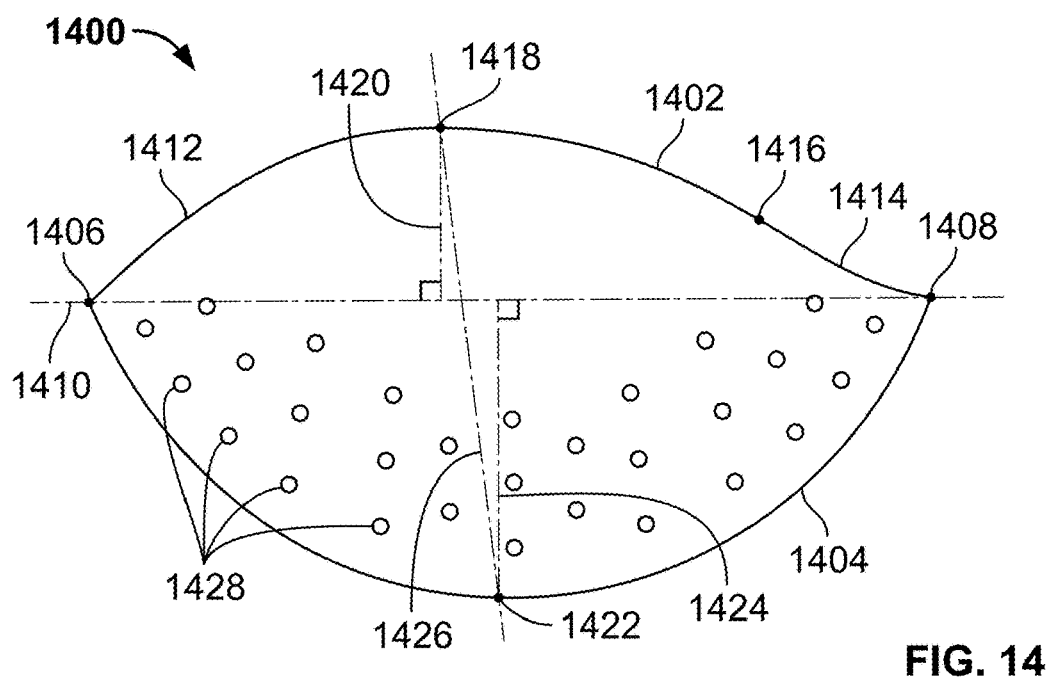
FIG. 14 is a top plan view of a second embodiment of an ACDM as adapted for use in breast reconstruction surgery.

FIG. 14 is a top plan view of an asymmetric tissue graft 1400 according to a further exemplary embodiment. The graft 1400 is similar to the asymmetric tissue graft 1200 other than insofar as will be described hereinafter. The asymmetric tissue graft 1400 includes a first peripheral edge 1402 and a second peripheral edge 1404. The first peripheral edge 1402 and second peripheral edge 1404 meet at a first vertex 1406 and a second vertex 1408. A first imaginary axis 1410 extends between the first vertex 1406 and the second vertex 1408. The first imaginary axis 1410 is an imaginary element defined herein for the purpose of describing the structure of the asymmetric tissue graft 1400, and it therefore is not a physical feature of the asymmetric tissue graft 1400.

Continuing to refer to FIG. 14, the first peripheral edge 1402 includes a convex portion 1412, which is convex with respect to (i.e., curves away from) the first axis 1410, and a concave portion 1414, which is concave with respect to (i.e., curves toward) the first axis 1410. A first point 1416 is located at the location where the convex portion 1412 of the first peripheral edge 1402 meets the concave portion 1414 of the first peripheral edge 1402. The second peripheral edge 1404 is convex, along its entire length with respect to (i.e., curves away from) the first axis 1410.

Continuing to refer to FIG. 14, the first peripheral edge 1402 includes an apogee 1418. An imaginary segment 1420 extends from the apogee 1418 to the first imaginary axis 1410 in a direction perpendicular to the first imaginary axis, and is longer than any of the other imaginary segments extending from every other point along the first peripheral edge 1402 to the first imaginary axis 1410 in a direction perpendicular to the first imaginary axis 1410. The apogee 1418 is located at a point along the length of the convex portion 1412 of the first peripheral edge 1402.

Continuing to refer to FIG. 14, the second peripheral edge 1404 includes an apogee 1422. An imaginary segment 1424 extends from the apogee 1422 to the first imaginary axis 1410 in a direction perpendicular to the first imaginary axis 1410, and is longer than any of the other imaginary segments extending from every other point along the second peripheral edge 1404 to the first imaginary axis 1410 in a direction perpendicular to the first imaginary axis 1410. A second imaginary axis 1426 extends through the apogee 1418 and the apogee 1422. The second imaginary axis 1426 is not perpendicular to the first imaginary axis 1410.

Continuing to refer to FIG. 14, the asymmetric tissue graft 1400 includes an array of perforations 1428. It should be noted that the exemplary asymmetric tissue graft 1400 includes twenty-nine (29) perforations 1428, but, for clarity of illustration, FIG. 14 annotates a subset of four (4) of the perforations shown as perforations 1428. It will be apparent to those of skill in the art that, in discussing the perforations 1428, the present disclosure refers to all perforations of the asymmetric tissue graft 1400. It will be further apparent to those of skill in the art that the specific quantity of perforations 1428 described herein and illustrated in FIG. 14 is only exemplary, and that the quantity of perforations 1428 may vary in other embodiments. In an embodiment, each of the perforations 1428 is substantially circular. In an embodiment, substantially all of the perforations 1428 are arrayed within the portion of the asymmetric tissue graft 1400 between the first axis 1410 and the second peripheral edge 1404.

The asymmetric tissue graft 1400, like the asymmetric tissue graft 1200, may be provided in a variety of sizes such that a surgeon performing a surgical breast procedure may choose an asymmetric tissue graft 1400 that is optimally sized for the patient, and correspondingly, does not need to cut a graft to size during a surgical procedure. In an embodiment, an appropriately sized asymmetric tissue graft 1400 may be selected based on the volume of an implant (e.g., a saline implant) to be supported by the asymmetric tissue graft 1400. In various embodiments, the asymmetric tissue graft 1400 may be provided in the same or similar sizes as those discussed above with reference to the asymmetric tissue graft 1200. It will be apparent to those of skill in the art that the quantity of perforations 1428 may vary for differently sized grafts 1400 (e.g., a larger size of an asymmetric tissue graft 1400 may have a greater quantity of perforations 1428 than a smaller size of an asymmetric tissue graft 1400).

Figure 15:
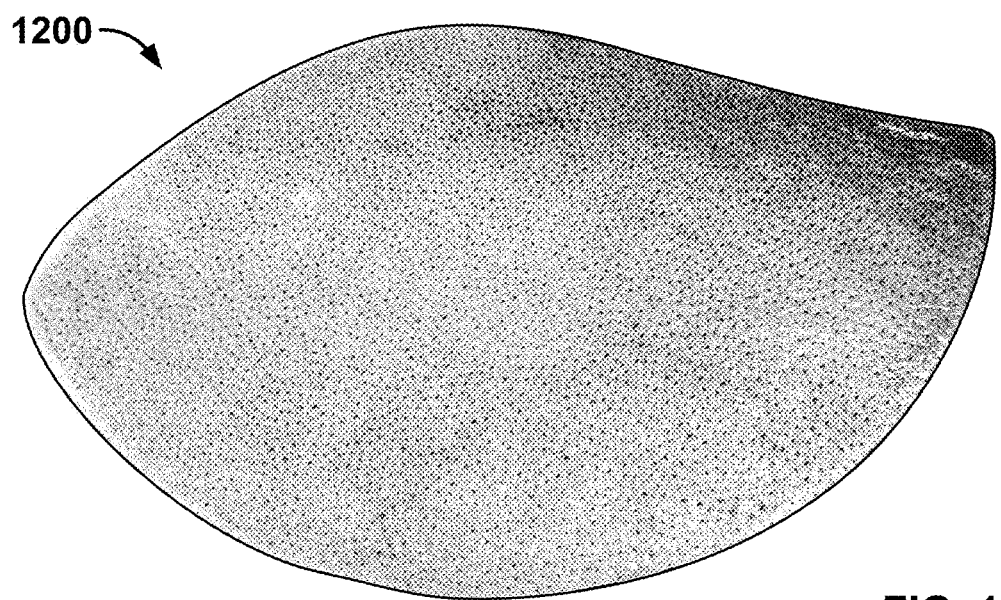
FIG. 15 is a photograph of the ACDM of FIG. 12.
Figure 16:
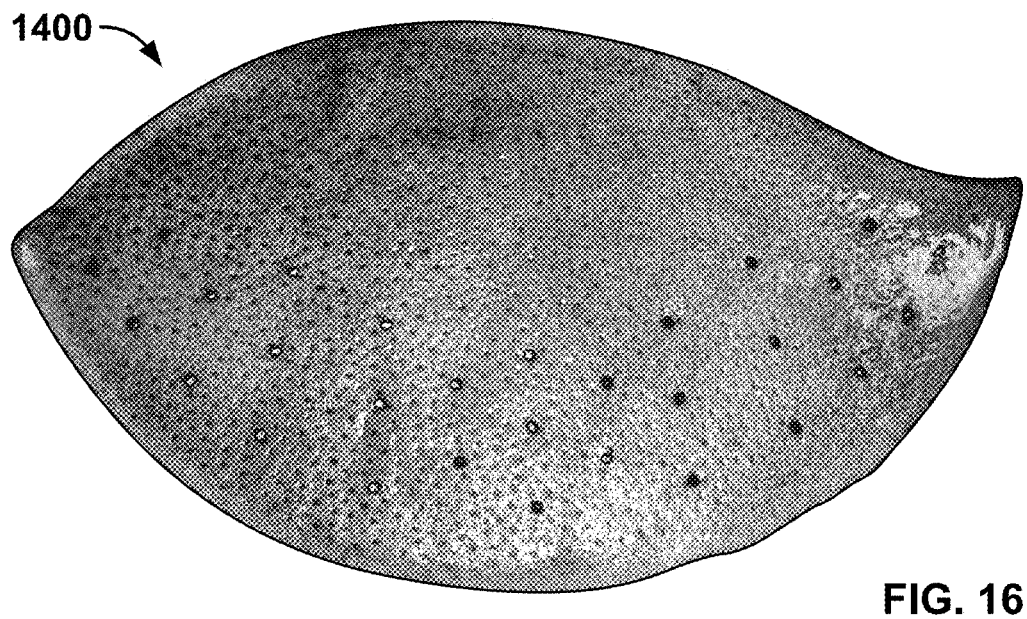
FIG. 16 is a photograph of the ACDM of FIG. 14.
Figure 17:
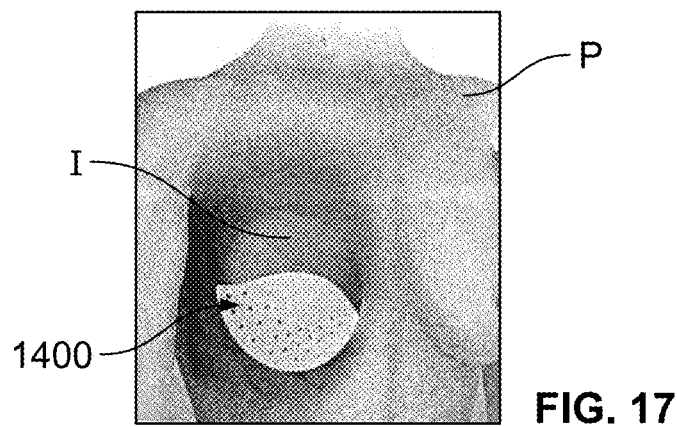
FIG. 17 is a perspective view of the ACDM of FIG. 14 being used as a sling for breast reconstruction according to an embodiment of the present invention.

FIG. 15 is a photograph of an exemplary asymmetric tissue graft 1200 as described above with reference to FIGS. 12 and 13. FIG. 16 is a photograph of an exemplary asymmetric tissue graft 1400 as described above with reference to FIG. 14. The exemplary grafts 1200, 1400 may be used in breast reconstruction surgery as a sling to support an implant (I) (e.g., a saline implant) during a breast reconstruction surgery performed on a patient (P). FIG. 17 is a rendering of the exemplary asymmetric tissue graft 1400 being used as a sling for breast reconstruction according to an embodiment of the present invention. The exemplary grafts 1200, 1400 provide improved coverage of the upper pole (i.e., the upper portion of the breast) as compared to prior art grafts; this may be particularly useful as skin in such areas is relatively thin and benefits from additional bulking and padding to support the weight of an implant. The exemplary grafts 1200, 1400 may be individually packaged, and may be provided singly or in kits of two such grafts for use in situations where reconstructive surgery is to be performed on both of a patient's breasts.

It will be known to those of skill in the art that a complication of breast reconstruction surgery, like any surgery in which tissue is removed, is a collection of excess fluid (i.e., seroma).

In the case of breast reconstruction surgery, such fluid may become trapped between a) an implant or tissue expander, and b) a graft supporting such implant or tissue expander. The perforations 1428 of the exemplary asymmetric tissue graft 1400, located in the lower portion of the asymmetric tissue graft 1400, allow for gravity to cause drainage of such fluid through the perforations 1428. Moreover, the inclusion of the perforations 1428 increases the surface area of the asymmetric tissue graft 1400; such an increase, coupled with the porosity of the tissue forming the asymmetric tissue graft 1400, may improve the incorporation of the asymmetric tissue graft 1400 into the recipient's body. Moreover, the perforations 1428 may improve the flexibility of the graft 1428 once it has been grafted implanted into the patient. While the perforations 1428 of the asymmetric tissue graft 1400 allow such benefits to be realized without the need for a surgeon to form such perforations prior to or during surgery, the exemplary asymmetric tissue graft 1200 without perforations allows surgeons to form a different alignment of perforations and/or slits (e.g., with a scalpel) in a desired manner and thereby realize similar benefits.

It should be understood that the embodiments of the invention described herein are merely exemplary and that a person skilled in the art may make many variations and modifications without departing from the spirit and scope of the invention. All such variations and modifications are intended to be included within the scope of the invention as defined herein.

We claim:

1. A dermal tissue allograft, comprising:
 a portion of dermal tissue having a first exposed surface and a second exposed surface, wherein said second exposed surface is opposite said first exposed surface, said portion of dermal tissue consisting of a portion of a papillary dermis and at least a portion of a reticular dermis, wherein the portion of the papillary dermis is a deeper portion distal an epidermis and adjacent the reticular dermis, wherein said deeper portion of said papillary dermis and said at least a portion of said reticular dermis have uniform density and porosity, whereby said portion of dermal tissue has uniform density and porosity between said first exposed surface and said second exposed surface, wherein said dermal tissue allograft has uniform density and porosity and lacks an epidermis, a dermis-epidermis junction, an upper epidermal portion of the papillary dermis, and a hypodermis, said dermal tissue having a profile including a first vertex, a second vertex, a first axis extending from said first vertex to said second vertex, a first peripheral edge extending along a continuous path from said first vertex to said second vertex on a first side of said first axis, and a second peripheral edge extending along a continuous path from said first vertex to said second vertex on a second side of said first axis, said second side being opposite to said first side, wherein said first peripheral edge includes an apogee that is a first perpendicular distance from said first axis, one convex portion that is convex with respect to said first axis, and one concave portion that is concave with respect to said first axis, said convex and concave portions of said first peripheral edge meeting at a transition point that is disposed on said first peripheral edge between said apogee of said first peripheral edge and said second vertex, wherein said transition point is the sole transition point disposed on the first peripheral edge, wherein said second peripheral edge includes an apogee that is a second perpendicular distance from said first axis, said second peripheral edge being convex with respect to said first axis, and said second perpendicular distance being greater than said first perpendicular distance, and wherein said dermal tissue has a thickness that is substantially uniform across said profile of said dermal tissue.

2. The dermal tissue allograft of claim 1, wherein said dermal tissue is an acellular dermal tissue.

3. The dermal tissue allograft of claim 1, wherein said dermal tissue includes a plurality of perforations.

4. The dermal tissue allograft of claim 3, wherein each of said plurality of perforations is substantially circular.

5. The dermal tissue allograft of claim 3, wherein the majority of said perforations are located between said first axis and said second peripheral edge.

6. The dermal tissue allograft of claim 1, wherein said apogee of said first peripheral edge and said apogee of said second peripheral edge define a second axis, and wherein said second axis is not perpendicular to said first axis.

7. The dermal tissue allograft of claim 1, wherein said first vertex and said second vertex have a distance between them, the distance being in a range from about 15 cm to about 24 cm.

8. The dermal tissue allograft of claim 7, wherein a ratio of the distance between said first vertex and said second vertex to said first perpendicular distance is in a range from about 4.2 to about 5.3.

9. The dermal tissue allograft of claim 7, wherein a ratio of the distance between said first vertex and said second vertex to said second perpendicular distance is in a range from about 2.4 to about 3.1.

10. The dermal tissue allograft of claim 1, wherein said first perpendicular distance is in a range from about 30 mm to about 55 mm.

11. The dermal tissue allograft of claim 1, wherein said second perpendicular distance is a range from about 60 mm to about 95 mm.

12. The dermal tissue allograft of claim 1, wherein a ratio of said second perpendicular distance to said first perpendicular distance is in a range from about 1.5 to about 2.1.

13. The dermal tissue allograft of claim 1, wherein said thickness of said dermal tissue is in a range from about 0.5 mm to about 3.0 mm.

14. A kit comprising two dermal tissue allografts as recited in claim 1.

* * * * *